(12) United States Patent
Yang et al.

(10) Patent No.: US 8,512,731 B2
(45) Date of Patent: Aug. 20, 2013

(54) ANTIMICROBIAL COATINGS FOR MEDICAL DEVICES AND METHODS FOR MAKING AND USING THEM

(75) Inventors: Zhongping Yang, Woodbury, MN (US); Eunjoo Jin, Los Angeles, CA (US); Laura Christoferson, Ramsey, MN (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 867 days.

(21) Appl. No.: 11/983,930

(22) Filed: Nov. 13, 2007

(65) Prior Publication Data
US 2010/0285084 A1 Nov. 11, 2010

(51) Int. Cl.
*A61K 38/43* (2006.01)
*A61K 38/44* (2006.01)

(52) U.S. Cl.
USPC .................. 424/423; 424/94.1; 424/94.4

(58) Field of Classification Search
None
See application file for complete search history.

(56) References Cited

U.S. PATENT DOCUMENTS

| | | | |
|---|---|---|---|
| 5,165,407 A * | 11/1992 | Wilson et al. | 600/345 |
| 5,770,060 A | 6/1998 | Ladisch et al. | |
| 5,786,439 A | 7/1998 | Van Antwerp et al. | |
| 6,287,285 B1 | 9/2001 | Michal et al. | |
| 6,358,556 B1 | 3/2002 | Ding et al. | |
| 6,475,434 B1 | 11/2002 | Darouiche | |
| 6,770,729 B2 | 8/2004 | Van Antwerp | |
| 7,813,780 B2 | 10/2010 | Shah et al. | |
| 2002/0037260 A1* | 3/2002 | Budny et al. | 424/49 |
| 2003/0031644 A1 | 2/2003 | Fitzpatrick et al. | |
| 2004/0074785 A1 | 4/2004 | Holker et al. | |
| 2005/0008671 A1* | 1/2005 | Van Antwerp | 424/423 |
| 2005/0272989 A1 | 12/2005 | Shah et al. | |
| 2006/0253085 A1 | 11/2006 | Geismar et al. | |
| 2007/0227907 A1 | 10/2007 | Shah et al. | |
| 2008/0026473 A1 | 1/2008 | Wang et al. | |

FOREIGN PATENT DOCUMENTS

| | | |
|---|---|---|
| FR | 2818150 | 6/2002 |
| WO | 98/26807 | 6/1998 |
| WO | 2005/018701 | 3/2005 |

OTHER PUBLICATIONS

EP Office Action dated May 3, 2011 (Application No. 08849279.8).
International Search Report, International application No. PCT/US2008/083395, International filing dated Nov. 13, 2008, mailed Feb. 24, 2010.

* cited by examiner

*Primary Examiner* — Robert A Wax
*Assistant Examiner* — Jessica Worsham
(74) *Attorney, Agent, or Firm* — Gates & Cooper LLP

(57) ABSTRACT

Embodiments of the invention provide methods for using compositions to inhibit microbial growth on a surface of a medical device having the composition applied thereto, to medical devices having the composition applied to a surface thereof and to methods for using the compositions to coat medical devices.

15 Claims, 6 Drawing Sheets

ANTIMICROBIAL COATINGS FOR MEDICAL DEVICES AND METHODS FOR MAKING AND USING THEM

CROSS REFERENCE TO RELATED APPLICATIONS

This application is related to U.S. patent application Ser. No. 10/273,767 filed Oct. 18, 2002 (published as US-2004-0074785-A1), U.S. patent application Ser. No. 10/616,784 filed Jul. 10, 2003; U.S. patent application Ser. No. 10/861,837, filed Jun. 4, 2004, U.S. patent application Ser. No. 11/149,119, filed Jun. 8, 2005, U.S. patent application Ser. No. 11/301,512, filed Dec. 13, 2005, U.S. patent application Ser. No. 11/397,543, filed Apr. 4, 2006, and U.S. patent application Ser. No. 11/492,273, filed Jul. 25, 2006, the contents of each of which are incorporated herein by reference.

BACKGROUND OF THE INVENTION

1. Field of the Invention

The present invention relates to antimicrobial compositions for coating medical devices. These compositions are used in methods designed to inhibit the growth of microorganisms and/or the formation of biofilms on the surfaces of such devices.

2. Description of Related Art

Infectious microorganisms such as bacteria, fungi and the like are capable of growing on a wide variety of living and non-living surfaces, including skin, teeth, mucosa, vascular tissue and medical devices including those implanted in-vivo. Individual microorganisms not attached to or growing on a surface are typically referred to as "planktonic". Planktonic organisms are responsible for a variety of localized and disseminated infections. When planktonic microorganisms grow and disseminate on non-living surfaces such as the surfaces of medical implants, they may cause contamination and biofouling of that surface. In many cases a microorganism can grow and accumulate on a surface to the point of becoming almost impossible to remove. This accumulation takes place through the formation of biofilms. A biofilm typically occurs when one or more microorganisms attach to a surface and secrete a hydrated polymeric matrix that surrounds them. Microorganisms existing in a biofilm, termed sessile, grow in a protected environment that insulates them from attack from antimicrobial agents. These sessile communities can give rise to nonsessile planktonic organisms, which rapidly multiply and disperse.

While planktonic organisms are typically killed by conventional antimicrobial treatments, these conventional treatments often fail to eradicate sessile communities rooted in biofilms. This is presumably due to the fact that the slime coat generated by the sessile film physically protects the underlying organisms by limiting diffusion to the organisms and often by chemical de-activation of the bacteriological agent. For this reason, biofilms are understood to be a frequently occurring reservoir for infectious agents and pose tremendous problems for the health-care industry. The biology of biofilms is described in more detail in Bacterial biofilms: a common cause of persistent infection" J. Costerson, P. Steward, E. Greenberg, Science 284: 1318-1322 (1999).

As noted above, infections associated with implanted medical devices typically involve biofilms, where the sessile community of the biofilm provides a reservoir for an invasive infection. Antibodies and other host immune defenses can be relatively ineffective in killing the organisms contained in a biofilm even though these organisms have elicited the antibody and related immune response. In addition, while antibiotics typically treat infections caused by the planktonic organisms, they are significantly less effective at killing the sessile organisms protected in the biofilm. Consequently, once a biofilm is established on an implant such as a medical device, it can be extremely difficult to treat the infection without actually removing and replacing the device. Unfortunately, even if the contaminated medical device is removed from the host, any replacement device will be particularly susceptible to contamination from the residual microorganisms in the area from which the medical device was removed.

As the difficulties associated with eliminating biofilm-based infections and contamination are well-recognized, a number of technologies have developed to prevent or impair microbial growth on the surface of medical devices. Unfortunately, microbial colonization of medical device surfaces continues to be a significant problem within the health care industry, in part due to ongoing difficulties in the ability to prevent organisms from establishing biofilms on the surfaces of medical devices. Consequently, there is a need in the art for methods and compositions that are effective in inhibiting the microbial growth on the surfaces of the wide variety of medical devices that are susceptible to microbial colonization and biofilm formation.

SUMMARY OF THE INVENTION

The invention disclosed herein relates generally to methods for using compositions to inhibit microbial growth on medical devices, medical devices having at least one surface coated with such compositions as well as methods for coating medical devices with these compositions. The properties of these compositions can be controlled to exhibit a number of characteristics including an ability to inhibit the growth of and/or kill pathogenic organisms.

The invention disclosed herein has a number of embodiments. A typical embodiment of the invention is a method of inhibiting the growth of a microorganism on a surface of an implantable medical device comprising coating the surface of the medical device with a first layer comprising an antimicrobial composition that includes a polypeptide that generates hydrogen peroxide upon exposure to a ligand for the polypeptide. Embodiments of the invention include implantable medical devices having a second layer comprising another antimicrobial and/or immunomodulatory and/or anti-inflammatory composition. For example, a second layer can comprise an antimicrobial composition that includes a polymer having a quaternary amine moiety (e.g. a polyurea-silicone copolymer), so that microbial growth is further inhibited on the surface of the medical device when the surface is exposed to a microorganism. Typically, such embodiments of the invention are used to inhibit the growth of one or more microorganisms capable of forming a biofilm on the surface of a medical device. Alternatively, a second layer can comprise an immunomodulatory agent such as a steroid (e.g. dexamethasone) which inhibits the in vivo inflammatory responses that can occur upon implantation of a medical device. Certain embodiments of the invention are used to inhibit the growth of *Pseudomonas aeruginosa, Streptococcus pneumoniae, Streptococcus viridans, Haemophilus influenzae, Escherichia coli, Staphylococcus aureus, Staphylococcus epidermidis* or *Candida albicans*. Some embodiments of the invention include the further step of identifying a susceptible surface on the medical device that is observed to be colonized in vivo by a microorganism when the device is implanted in a mammal, coating at least 95% of this susceptible surface with the one or more antimicrobial layers, and then implanting the medical device in a mammal so that in vivo microbial growth is inhibited. Some embodiments of the invention can be used to inhibit the growth of a microorganism on the surface of the medical device that is implanted in an individual having a pathological condition characterized by hyperglycemia, for example diabetes. Other embodiments of the invention can be used to inhibit the growth of a microorganism on the surface of the medical device that is implanted in an individual having a pathological condition characterized by ischemia, for example heart disease.

Embodiments of the above-noted methods can be used to dispose a variety of antimicrobial compositions on to a variety of surfaces. In certain embodiments of the invention for example, the surface of the medical device coated by the methods of the invention comprises titanium. Alternatively, the surface of the medical device coated by the methods of the invention can comprise another metal such as stainless steel, and/or derivatives or combinations of those metals typically found at the surface of medical devices. Alternatively, the surface can comprise non-metallic materials such as a thermoplastic and/or a polymeric material. In typical embodiments of this invention, the medical device (and/or individual component of a medical device) coated by these methods is an implantable medical device such as an analyte sensing device (e.g. a glucose sensor), a medication infusion apparatus (e.g. an insulin infusion pump) or a cardiac management device (e.g. a pacemaker or cardiovertor defibrillator). In one specific illustrative embodiment, the medical device is a glucose sensor comprising a plurality of layers, wherein at least one of the layers comprises an electrode having an electrochemically reactive surface area, an analyte sensing layer that detectably alters the electrical current at the electrode in the presence of an analyte, an adhesion promoting layer that promotes the adhesion between one or more layers of the glucose sensor, an analyte modulating layer that modulates the diffusion of a analyte therethrough, and/or a cover layer that is impermeable to blood glucose.

In typical embodiments of the invention, the polypeptide in the first layer is an oxidoreductase such as glucose oxidase or lactate oxidase and the polymeric composition in the second layer is an antimicrobial composition (e.g. polyurea-silicone copolymer) or a immunomodulatory composition (e.g. dexamethasone). Certain embodiments of the methods further include disposing one or more further layers proximal to, distal to, on top of, below or between the first layer and the second layer. Such further layers can include for example a composition disposed between the first and second layer that promotes adhesion and/or a composition disposed on top of the first and second layers that functions as an insulating protective cover layer for the medical device. In certain embodiments of the invention, a further layer coated onto the surface of the medical device comprises a biodegradable polymer. In some embodiments of the invention, these layers include further bioactive components, for example an antibiotic, a lectin or an anti-inflammatory composition.

Another illustrative embodiment of the invention is a method for inhibiting the formation of a biofilm on a medical device that is implanted in an individual suffering from a condition characterized by hyperglycemia (for example diabetes). Yet another illustrative embodiment of the invention is a method for inhibiting the formation of a biofilm on a medical device that is implanted in an individual suffering from a condition characterized by ischemia (for example heart disease). In such embodiments of the invention, the method comprises identifying a surface on the medical device that is observed to be colonized by a biofilm forming microorganism, and then coating this surface with a first layer that comprises an antimicrobial composition that includes a oxidoreductase (e.g. glucose oxidase or lactate oxidase) that generates hydrogen peroxide upon exposure to an in vivo ligand (e.g. glucose or lactate), wherein the amount of hydrogen peroxide generated by the polypeptide is proportional to the amount of ligand exposed to the polypeptide. In certain embodiments of the invention, the medical device is also coated with second layer disposed over the first layer that comprises an antimicrobial composition and/or an anti-inflammatory composition. The multiple layers are disposed on the medical device in this way so that formation of a biofilm on the medical device is inhibited when the surface is exposed to the biofilm forming microorganism. In typical embodiments of this invention, the medical device (and/or element of a medical device) coated by these methods is an implantable medical device such as an analyte sensing device (e.g. a glucose sensor), a medication infusion apparatus (e.g. an insulin infusion pump) or a cardiac management device (e.g. a pacemaker or cardiovertor defibrillator).

Typically in such embodiments of the invention, the oxidoreductase in the first layer is glucose oxidase or lactate oxidase and the method further comprises immobilizing the oxidase on the surface of the medical device using a procedure that results in the oxidase having a oxidoreductase activity that is at least equal to the oxidoreductase activity observed when the oxidase is immobilized on the surface via glutaraldehyde crosslinking. Optionally in some embodiments of the invention, a second antimicrobial layer is formed from a reaction mixture comprising a diisocyanate, a hydrophilic polymer which is a member selected from the group consisting of a hydrophilic polymer diol, a hydrophilic polymer diamine and combinations thereof; and a siloxane. Certain embodiments of the invention include coating additional layers on the medical device, for example coating the medical device with a biodegradable polymer that is observed to degrade or erode at a predetermined rate within an in vivo environment.

Another embodiment of the invention is a method of inhibiting microbial growth on a medical device that is implanted in a diabetic individual, the method comprising coating a surface of the medical device with at least two antimicrobial compositions, wherein the antimicrobial compositions include a first layer comprising a glucose oxidase composition, wherein the glucose oxidase is disposed in the first layer so as to generate hydrogen peroxide upon exposure to glucose in the individual; and the first layer is disposed on the device so as to allow hydrogen peroxide generated by the glucose oxidase in the first layer to diffuse away from the glucose oxidase and contact a microorganism attempting to grow on the medical device and inhibit its growth; wherein the amount of hydrogen peroxide generated by the glucose oxidase fluctuates in response to fluctuating glucose levels within the individual; and an optional second layer comprising a polyurea-silicone copolymer composition having a quaternary amine, wherein the second layer is disposed on the medical device in a location such that the quaternary amine in the second layer inhibits the growth of a microorganism that contacts the second layer, so that microbial growth on the implanted medical device is inhibited.

Another embodiment of the invention is a method of inhibiting formation of a biofilm on a medical device that is implanted in an individual having a pathological condition characterized by ischemia (e.g. heart disease), the method comprising identifying a surface on the medical device that is observed to be colonized by a biofilm forming microorganism; and then coating the surface with a first layer that comprises an antimicrobial composition that includes a oxidoreductase that generates hydrogen peroxide upon exposure to a ligand for the oxidoreductase; so that formation of a biofilm on the medical device is inhibited when the surface is exposed to the biofilm forming microorganism. Typically, the oxidoreductase is lactate oxidase which is disposed on the medical device in a location such that hydrogen peroxide generated by the lactate oxidase fluctuates in response to fluctuating lactate levels within the individual; and hydrogen peroxide generated by the lactate oxidase diffuses away from the lactate oxidase and contacts a microorganism attempting to grow on the medical device so as to inhibit its growth. In certain embodiments of the invention, the method further comprises inhibiting an anti-inflammatory response in the individual in which the device is implanted by coating the medical device with a second layer that comprises an anti-inflammatory steroid composition. In typical embodiments of the invention, the surface on the medical device is that found on a cardiac management system, for example an electronic lead of a pacemaker.

Yet another embodiment of the invention is an implantable medical device having a surface coated with an antimicrobial composition that includes a oxidoreductase disposed on the device (e.g. lactate oxidase) that generates hydrogen peroxide upon exposure to a ligand (e.g. lactate), wherein the antimicrobial composition is disposed on the surface of the device so as to allow hydrogen peroxide generated by the oxidoreductase to diffuse away from the oxidoreductase and contact a microorganism attempting to grow on the medical device, thereby inhibiting the growth of the microorganism. In certain embodiments, a surface of the medical device is further coated with a second layer having another bioactive agent, for example a dexamethasone composition. Typically the surface of the medical device is that found on a cardiac management system, for example an electronic lead of a pacemaker.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

Referring now to FIG. 4A, the surface of the medical device is represented by the numeral 20. The surface 20 includes a first polymer matrix 22, within which is disposed a lectin 24 capable of binding a biofilm compound and/or a biofilm forming organism. The surface 20 includes a second polymer matrix 26, within which is disposed one or more agents 28 that are capable of inhibiting the growth of the microorganism. Typically the agent 28 is a broad-spectrum antibiotic agent. As shown in FIG. 4B, the lectin 24 recognizes and binds a biofilm (and/or a biofilm forming organism) 30. As shown in FIG. 4B, this lectin-biofilm interaction can be used to localize the biofilm forming organism to a region of the surface 20 having one or more agents 28 that are capable of inhibiting the growth of the biofilm forming organism. As shown in FIG. 4C, the first polymer matrix 22 can be biodegradable so that the biofilm 30 bound by the lectin 24 sloughs away from the surface 20 of the medical device. In the embodiment of the invention shown in FIG. 4C, the second polymer matrix 26 having the agent 28 can be substantially nonbiodegradable so that the agent 28 remains at the surface of the medical device.

DETAILED DESCRIPTION OF TYPICAL EMBODIMENTS

Figure 1:
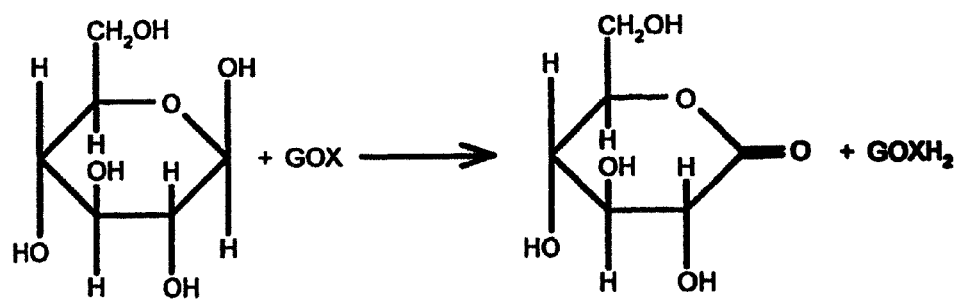
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid.
Figure 1:
Figure 1:
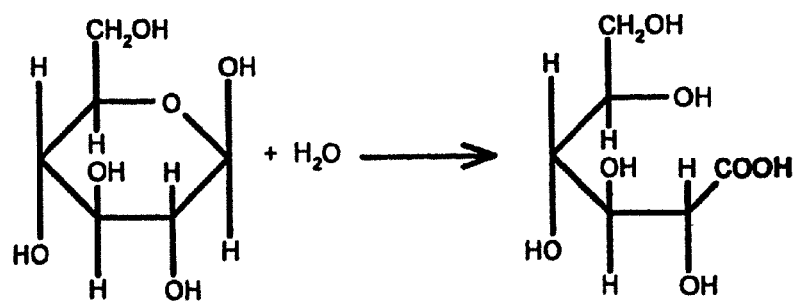
Figure 2:
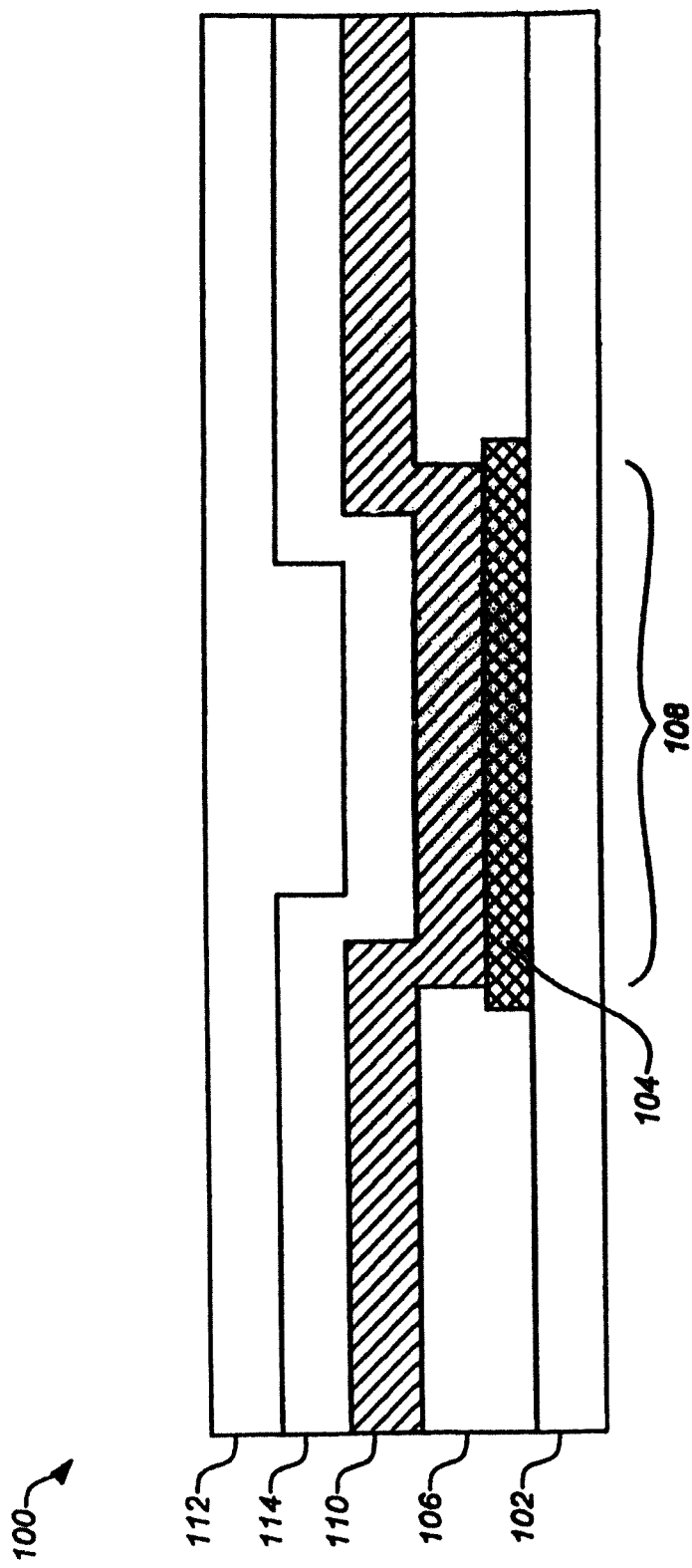
FIG. 2 provides a diagrammatic view of a typical analyte sensor configuration which can be coated with the layered compositions of the current invention.

Unless otherwise defined, all terms of art, notations and other scientific terms or terminology used herein are intended to have the meanings commonly understood by those of skill in the art to which this invention pertains. In some cases, terms with commonly understood meanings are further defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as those described in see Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

Embodiments of the invention disclosed herein provide compositions for coating medical devices, medical devices having at least one surface coated with such compositions as well as methods for coating medical devices with these compositions. The properties of these compositions are controlled to exhibit a number of characteristics including an ability to inhibit the growth organisms such as planktonic organisms (e.g. via molecules such as antimicrobial polypeptides and/or antimicrobial quaternary amine compounds). In accordance with a typical embodiment of the present invention, a method is disclosed to provide an implantable medical device with a coating which inhibits the growth and thereby facilitates the clearance of one or more biofilm forming organisms. The term "biofilm" is used according to its art accepted meaning and refers to microorganisms and the extracellular polymeric substance (EPS) matrix that they generate on living and non-living surfaces as a method of cell immobilization for the microbial population(s). Briefly, as is well known in the art, microorganisms attach to surfaces and develop biofilms. Biofilm-associated cells are typically differentiated from their planktonic counterparts by generation of an extracellular polymeric substance (EPS) matrix, reduced growth rates, and the up- and down-regulation of specific genes. Attachment to a surface is a complex process regulated by diverse characteristics of the growth medium, substratum, and cell surface. An established biofilm structure typically comprises microbial cells and EPS, has a defined architecture, and provides an optimal environment for the exchange of genetic material between cells. Biofilms have great importance for public health because of their role in certain infectious diseases and importance in a variety of device-related infections. See, e.g. Donlan, Emerg Infect Dis 2002 September; 8(9):881-90.

Broadly, the biofilm inhibiting coatings of the invention typically include and antimicrobial oxidoreductase (e.g. glucose oxidase or lactate oxidase) that produces the antimicrobial compound hydrogen peroxide upon exposure to a substrate present in the environment in which a device is used (e.g. glucose or lactate). In certain embodiments, the biofilm inhibiting coatings further include antimicrobial quaternary amine compounds which inhibit biofilm formation on at least one surface of the medical device; and/or inhibits the growth or proliferation of biofilm microorganisms on at least one surface of the medical device. The biofilm inhibiting coatings for medical devices may be formulated to substantially prevent the colonization of the device by biofilm forming microorganisms, for example by killing and/or removing substantially all of the microorganisms on the surface of medical devices. "Biofilm microorganisms" include any one of the wide variety of microorganisms which form biofilms during colonization and proliferation on the surface of medical devices, including, but not limited to, gram-positive bacteria (such as *Staphylococcus epidermidis*), gram-negative bacteria (such as *Pseudomonas aeruginosa*), and/or fungi (such as *Candida albicans*). Typical embodiments of the invention typically target organisms including Pseudomonad species (e.g. *Pseudomonas aeruginosa* etc.) *Streptococcus* species (e.g. *Streptococcus pneumoniae, Streptococcus viridans* etc.), *Haemophilus* species (e.g. *Haemophilus influenzae* etc.), *Escherichia* species (e.g. *Escherichia coli* etc.) Enterobacteriaceae (e.g. *Enterobacter cloacae* etc.), *Proteus* species (e.g. *Proteus vulgaris* etc.) *Staphylococcus* species (e.g. *Staphylococcus aureus, Staphylococcus epidermidis* etc.), *Blastomonas, Sphingomonas, Methylobacterium* and *Nocardioides* species as well as yeast species such as *Candida albicans* etc.

Embodiments of the invention include methods wherein a medical device is coated with bioactive agents such as antimicrobial polypeptides and/or antimicrobial quaternary amine compounds so as to inhibit microbial growth on the surface of a device. As microbial growth on the surface of a device can lead to the formation of biofilms on the device as discussed above, embodiments of the invention that inhibit microbial growth consequently inhibit the formation of biofilms. Embodiments of the invention are directed to methods that inhibit biofilm microorganisms from effectively colonizing (e.g. growing and proliferating) at least one surface of the medical devices by coating the device with one or more antimicrobial compositions. In these contexts, artisans will understand that such coatings may include multiple layers of materials having one or more of the agents and/or properties disclosed herein. An illustrative embodiment of the invention is a method of inhibiting growth of a microorganism on a surface of a medical device by identifying a surface on the medical device that is observed to be colonized by a microorganism; and then coating this surface with a first layer comprising an antimicrobial composition that includes a polypeptide that generates hydrogen peroxide upon exposure to ligand for the oxidoreductase and optionally a second layer comprising an antimicrobial composition comprising a polymer having a quaternary amine moiety or anti-inflammatory agent disposed within; so that microbial growth is inhibited.

As noted above, embodiments of the invention include an antimicrobial layer comprising an enzyme (typically an oxidoreductase such as glucose oxidase or lactate oxidase) that releases hydrogen peroxide when exposed to its cognate ligand (e.g. glucose or lactate). In this context, the term "ligand" is used according to its art accepted meaning and refers to a typically smaller molecule (e.g. glucose or lactate) which binds to a another molecule such as an enzyme or protein (e.g. glucose oxidase or lactate oxidase), and is typically transformed into or produces something else through this binding process (e.g. hydrogen peroxide). Such embodiments of the invention can be used, for example to coat a medical device that is implanted within an individual, for example a glucose sensor that is implanted within a diabetic patient and/or a pacemaker system that is implanted in a patient with heart disease. In this context, because the amount of hydrogen peroxide produced by a oxidoreductase upon exposure to its ligand is proportional to the amount of ligand that reacts with the oxidoreductase, antimicrobial layers comprising an oxidoreductase enzyme specific to such substrate for producing hydrogen peroxide function as an "intelligent release layer" where levels of the hydrogen peroxide antimicrobial compound generated by the oxidoreductase will fluctuate in response to fluctuating ligand levels. Certain embodiments of the invention are designed to take advantage of this characteristic of these layers by selectively disposing the a device coated with such layers in an environment where fluctuating levels of an ligand such as glucose or lactate are correlated with risk of infection (e.g. implantation within a diabetic individual or an individual with heart disease).

Embodiments of the invention are predicated on the interactions between oxidoreductases and their in vivo ligands. FIG. 1 for example provides a schematic of an embodiment of the invention that is predicated on the reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In this context, it is known in the art that enzymatic anti-bacterial systems, predicated on oxidoreductase enzymes such as glucose oxidase, can be used in a variety of contexts (see, e.g. U.S. Pat. No. 4,617,190, U.S. Pat. No. 4,150,113, U.S. Pat. No. 4,269,822 U.S. Pat. No. 4,178,362 and U.S. Pat. No. 4,576,817, the contents of which are incorporated by reference) in order to produce an anti-bacterial effect in a defined environment. An illustrative listing of polypeptides that generate $H_2O_2$ appears in Clark et al. Biotechnol. Bioeng. Symp. 3: 377 (1972). These polypeptides include: lactate oxidase, pyruvate oxidase, xanthine oxidase, sarcosine oxidase, lipoamide dehydrogenase, glutathione reductase, aldehyde oxidase, glucose oxidase, glycollate oxidase, L-amino oxidase, galactose oxidase (see also U.S. Pat. No. 4,830,011, the contents of which are incorporated by reference).

The use of polypeptide oxidoreductases such as lactate oxidase for analyzing lactic acid and lactate levels is well known in the art. For example, U.S. Pat. No. 4,166,763 teaches various ways that the oxidoreductase lactate oxidase for use in analysis of lactate or lactic acid whereby the lactic acid is oxidized to produce pyruvate and hydrogen peroxide. In this context, the level of lactic acid in the blood is an indicator of the adequacy of blood circulation and is a biochemical criterion of the severity of circulatory failure in which increased lactate levels are observed. Lactate (e.g. a salt or ester of lactic acid) can be measured for the diagnosis, quantitation of the severity, and prognosis of shock states. It is also an indicator of prognosis in acute myocardial infarction and myocardial failure. In sports medicine and exercise physiology, blood lactate levels measure anaerobic capacity and can be used to evaluate the effectiveness of training, predict endurance and detect over-training. Also lactate and pyruvate levels increase rapidly in normal individuals following administration of glucose or injection of insulin. This rise is delayed or absent in diabetes mellitus. So determinations of both lactate and glucose concentrations can be used to distinguish between pancreatic diabetes and other disorders exhibiting decreased glucose tolerance.

In addition to a layer comprising an oxidoreductase, certain embodiments of the invention include medical devices having another antimicrobial layer comprising a silicon-containing copolymer that includes a quaternary ammonium moiety. Silicon-containing quaternary ammonium moiety antimicrobial agents belong to a general class of antimicrobial agents termed cationic antimicrobial agents. As used herein, an "antimicrobial agent" is an agent that inhibits the growth of and/or kills microorganisms, and particularly pathogenic microorganisms. The use of a number of quaternary ammonium compounds as antimicrobial agents is described the art (see, e.g., Gottenbos et al., Biomaterials 2002, 23(6): 1417-1423; Lee et al., 2004, 5(3): 877-882; e.g., U.S. Pat. Nos. 3,560,385; 3,794,736; 3,814,739; U.S. Pat. Nos. 3,730,701; 3,794,736; 3,860,709; 4,282,366; 4,394,378; 4,408,996; 4,414,268; 4,504,541; 4,615,937; 4,620,878; 4,631,273; 4,692,374; 4,842,766; 5,064,613; 5,358,688; 5,359,104; 5,411,585; 5,954,869; 5,959,014; 6,113,815; 6,120,587; 6,146,688 and 6,572,926; 6,221,944; 6,469,120; 6,632,805; and 6,762,172 as well as U.S. Patent Application No. 20060223962; the disclosures of which are incorporated herein by reference).

As noted above, the invention disclosed herein relates generally to methods for using compositions to inhibit microbial growth on medical devices, medical devices having at least one surface coated with such compositions as well as methods for coating medical devices with these compositions. The properties of these compositions can be controlled to exhibit a number of characteristics including an ability to inhibit the growth of and/or kill pathogenic organisms. A typical embodiment of the invention is a method of inhibiting the growth of a microorganism on a surface of a medical device comprising coating the surface of the medical device with a first layer comprising an antimicrobial composition that includes a polypeptide that generates hydrogen peroxide upon exposure to a ligand and typically a second layer comprising an antimicrobial composition comprising a polymer having a quaternary amine moiety and/or an anti-inflammatory agent disposed therein, so that microbial growth is inhibited on the surface of the medical device when the surface is exposed to a microorganism and/or an anti-inflammatory response is inhibited in the subject in which the device is implanted. As noted above, a number of polypeptides that generate hydrogen peroxide are known in the art and include for example glucose oxidase, lactate oxidase, glutamate oxidase and L-alpha-glycerol-phosphate oxidase etc. Typically, the methods of the invention are used to inhibit the growth of a microorganism that is capable of forming a biofilm on the surface of a medical device. Certain embodiments of the invention are used to inhibit the growth of *Pseudomonas aeruginosa, Streptococcus pneumoniae, Streptococcus viridans, Haemophilus influenzae, Escherichia coli, Staphylococcus aureus, Staphylococcus epidermidis* or *Candida albicans*.

Some embodiments of the invention include the further step of identifying a susceptible surface on the medical device that is observed to be colonized in vivo by a microorganism when the device is implanted in a mammal, coating at least 75, 80, 85, 90 or 95% of this susceptible surface with the first and second layers, and then implanting the medical device in a mammal so that in vivo microbial growth is inhibited. In certain embodiments of the invention, such methods of the invention can be used to inhibit the growth of a microorganism on the surface of the medical device that is implanted in an individual having a pathological condition characterized by hyperglycemia, for example diabetes. In other embodiments of the invention, such methods of the invention can be used to inhibit the growth of a microorganism on the surface of the medical device that is implanted in an individual having a pathological condition characterized by ischemia, for example heart disease. As is known in the art, the term "heart disease" refers to those disorders that affects the heart muscle or the blood vessels of the heart (e.g., arrhythmia, coronary heart disease, coronary artery disease, dilated cardiomyopathy, heart attack, heart failure, hypertrophic cardiomyopathy, mitral regurgitation, pulmonary stenosis and the like). Medical devices coated with the compositions disclosed herein are particularly useful for long-term indwelling applications due to their ability to resist biofilm formation and encrustation. As used herein, "long-term" is greater than 3 months, and typically greater than 6 months and more typically greater than 1 year. Subjects for treatment via implantation are typically mammalian subjects and more typically human subjects.

Embodiments of the above-noted methods can be used to dispose a variety of antimicrobial compositions on to a variety of surfaces. In certain embodiments of the invention for example, the surface of the medical device coated by the methods of the invention comprises titanium. Alternatively, the surface of the medical device coated by the methods of the invention can comprise another metal such as stainless steel, and or derivatives or combinations of those metals typically found at the surface of a medical device. Alternatively, the surface can comprise non-metallic materials such as a thermoplastic and/or a polymeric material. In typical embodiments of this invention, the medical device (and/or element of a medical device) coated by these methods is an implantable medical device such as an analyte sensing device (e.g. a glucose sensor), a medication infusion apparatus (e.g. an insulin infusion pump) or a cardiac management device (e.g. a pacemaker or cardiovertor defibrillator). In one specific illustrative embodiment, the medical device is a glucose sensor comprising a plurality of layers, wherein at least one of the layers comprises an electrode having an electrochemically reactive surface area, an analyte sensing layer that detectably alters the electrical current at the electrode in the presence of an analyte, an adhesion promoting layer that promotes the adhesion between one or more layers of the glucose sensor, an analyte modulating layer that modulates the diffusion of a analyte therethrough, and/or a cover layer that is impermeable to blood glucose.

In some embodiments of the invention, the polypeptide in the first layer is glucose oxidase and the polymeric composition in the second layer is a polymer formed from a reaction mixture of a diisocyanate, a hydrophilic polymer, and a hydrophilic silicone. Certain embodiments of the methods further include disposing one or more further layers on top of, below or between the first layer and the second layer. Such further layers can include for example a composition disposed between the first and second layer that promotes adhesion and/or a composition disposed on top of the first and second layers that functions as an insulating protective cover layer for the medical device. In certain embodiments of the invention, a further layer coated onto the surface of the medical device comprises a biodegradable polymer. In some embodiments of the invention, these layers include further bioactive components, for example an antibiotic, a lectin or an anti-inflammatory composition.

Another illustrative embodiment of the invention is a method for inhibiting the formation of a biofilm on a medical device that is implanted in an individual suffering from a condition characterized by hyperglycemia (for example diabetes). In this embodiment of the invention, the method comprises identifying a surface on the medical device that is observed to be colonized by a biofilm forming microorganism, and then coating this surface with a first layer that comprises an antimicrobial composition that includes a oxidoreductase that generates hydrogen peroxide upon exposure to an in vivo ligand of the oxidoreductase, wherein the amount of hydrogen peroxide generated by the oxidoreductase is proportional to the amount of ligand to which it is exposed. In this embodiment of the invention, the medical device is typically coated with second layer disposed over the first layer that comprises an antimicrobial composition comprising for example a polyurea-silicone copolymer. The multiple layers are disposed on the medical device in this way so that formation of a biofilm on the medical device is inhibited when the surface is exposed to the biofilm forming microorganism. In typical embodiments of this invention, the medical device (and/or element of a medical device) coated by these methods is an implantable medical device such as an analyte sensing device (e.g. a glucose sensor), a medication infusion apparatus (e.g. an insulin infusion pump) or a cardiac management device such as a pacemaker or cardiovertor defibrillator (e.g. the electrodes of a pacemaker lead). A related embodiment of the invention is a method of inhibiting microbial growth on a medical device that is implanted in a diabetic individual, the method comprising coating a surface of the medical device with at least two antimicrobial compositions, wherein the antimicrobial compositions include: a first layer comprising a glucose oxidase composition, wherein the glucose oxidase generates hydrogen peroxide upon exposure to glucose in the individual and the amount of hydrogen peroxide generated by the glucose oxidase fluctuates in response to fluctuating glucose levels within the individual; and a second layer comprising a polyurea-silicone copolymer composition.

Another illustrative embodiment of the invention is a method for inhibiting the formation of a biofilm on a medical device that is implanted in an individual suffering from a condition characterized by ischemia (for example heart disease). In this embodiment of the invention, the method comprises identifying a surface on the medical device that is observed to be colonized by a biofilm forming microorganism, and then coating this device with a first layer that comprises an antimicrobial composition that includes a oxidoreductase (e.g. lactate oxidase) that generates hydrogen peroxide upon exposure to its cognate ligand (e.g. lactate), wherein the amount of hydrogen peroxide generated by the polypeptide is proportional to the amount of ligand exposed to the oxidoreductase. In some embodiments of the invention, the medical device is also coated with second layer that comprises an antimicrobial and/or anti-inflammatory composition, for example one comprising a polymeric composition impregnated with dexamethasone. The multiple layers are disposed on the medical device in this way so as to: (1) inhibit formation of a biofilm on the medical device when the surface is exposed to the biofilm forming microorganism; and (2) inhibit an inflammatory response associated with implantation when the surface is exposed immune cells within the subject in which the device is implanted. In typical embodiments of this invention, the medical device (and/or element of a medical device) coated by these methods is a cardiac management device such as a pacemaker or cardiovertor defibrillator (e.g. the electrodes of a pacemaker lead).

In certain embodiments of the invention, the antimicrobial activity of an oxidoreductase such as glucose oxidase or lactate oxidase can be manipulated in a control way via different surface immobilization techniques of the oxidase on implantable medical devices. In particular, the oxidoreductase can be immobilized within a layer disposed on a medical device via a number of different techniques and the specific technique used can influence the antimicrobial activity of the immobilized polypeptide. In this context, a wide variety of such immobilization techniques are known in the art (see, e.g. U.S. Pat. No. 4,894,339; Liu et al., Anal Chem. 1997 Jul. 1; 69(13):2343-8; Inman et al., Biochem J. 1972 September; 129(2):255-62; Shan et al., Biosens Bioelectron. 2007 Mar. 15; 22(8):1612-7, Epub 2006; Salimi et al., Biosens Bioelectron, 2007 Jun. 15; 22(12):3146-53, Epub 2007; and Wu et al., Biosens Bioelectron. 2007 Jun. 15; 22(12):2854-60, Epub 2007, the contents of which are incorporated by reference). Typically in such embodiments of the invention, the oxidoreductase in the first layer is glucose oxidase or lactate oxidase and the method further comprises immobilizing the glucose oxidase or lactate oxidase on the surface of the medical device using a procedure that results in the glucose oxidase or lactate oxidase having a oxidoreductase activity that is at least equal to the oxidoreductase activity observed when the glucose oxidase or lactate oxidase is immobilized on the surface via glutaraldehyde crosslinking.

In some embodiments of the invention, a second layer disposed on a medical device is formed from a reaction mixture comprising a diisocyanate, a hydrophilic polymer which is a member selected from the group consisting of a hydrophilic polymer diol, a hydrophilic polymer diamine and combinations thereof; and a siloxane. In one illustrative embodiment of the invention, the polymer is a polyurea-silicone copolymer which comprises a diisocyanate such as 4,4-methylenebis(cyclohexyl isocyanate), a hydrophilic diamine such as O,O'-Bis(2-aminopropyl) polypropylene glycol-block polyethylene glycol-block-polypropylene glycol and a hydrophobic silicone such as bis(3-aminopropyl) terminated poly(dimethylsiloxane). Certain embodiments of the invention include coating additional layers on the medical device, for example coating the medical device with a biodegradable polymer that is observed to degrade at a predetermined rate within an in vivo environment. In other embodiments of the invention, a second layer disposed on a medical device is formed from a reaction an immunomodulatory and/or anti-inflammatory agent such as a steroid blended with a polymeric material, for example dexamethasone impregnated within a silicone polymer, a blended composition that is designed to slowly elute the steroid out of the polymer and into the surrounding tissue.

One embodiment of the invention is a method of inhibiting microbial growth on the surface of a medical device that is designed to be implanted and/or is implanted in an individual having a syndrome characterized by hyperglycemia such as diabetes (e.g. a glucose sensor and/or a insulin infusion device). In particular, it is observed in the art that in diabetic patients undergoing surgical procedures, preoperative hyperglycemia is an independent predictor of short term infectious complications and total length of stay in hospital and further that postoperative glucose control predicts nosocomial infection rate in these patients (see, e.g. Pomposelli et al., J. Parenter. Enteral. Nutr. 1998, 22(2): 77-81; Ann. Thorac. Surg. 1999, 67(2): 352-360; and Guvener et al., Endocrine Journal 2002, 49(5): 531-537. Consequently, certain methodological embodiments of the invention are designed for implantation in hyperglycemic individuals because the higher levels of glucose in such individuals will correspondingly result in GOx within the layers generating higher levels of hydrogen peroxide and in this way counteract the increased risk of infection that is associated with elevated blood sugar levels.

Another embodiment of the invention is a method of inhibiting formation of a biofilm on a medical device that is implanted in an individual having a pathological condition characterized by ischemia (e.g. heart disease), the method comprising identifying a surface on the medical device that is observed to be colonized by a biofilm forming microorganism; and then coating the surface with a first layer that comprises an antimicrobial composition that includes a oxidoreductase that generates hydrogen peroxide upon exposure to a ligand for the oxidoreductase (e.g. lactate oxidase); so that formation of a biofilm on the medical device is inhibited when the surface is exposed to the biofilm forming microorganism. Typically, the oxidoreductase is lactate oxidase which is disposed on the medical device in a location such that hydrogen peroxide generated by the lactate oxidase fluctuates in response to fluctuating lactate levels within the individual; and hydrogen peroxide generated by the lactate oxidase diffuses away from the lactate oxidase and contacts a microorganism attempting to grow on the medical device so as to inhibit its growth.

In certain embodiments of the invention, the method further comprises comprising inhibiting a physiological response to the implanted medical device (e.g. anti-inflammatory response) in the individual having a pathological condition characterized by ischemia (e.g. heart disease). In such embodiments, the implanted medical device is coated with a second layer that comprises an agent known to modulate an individuals physiological response to the implanted device, for example a glucocorticoid such as dexamethasone, dexamethasone sodium phosphate, dexamethasone acetate or another dexamethasone derivative as well as related molecules such as beclamethasone or betamethasone. Other agents useful for such embodiments of the invention include heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents (see, e.g. U.S. Pat. No. 6,203,536, the contents of which are incorporated by reference). In typical embodiments of the invention, the surface on the medical device is that found on a cardiac management system, for example an electronic lead of a pacemaker.

Yet another embodiment of the invention is an implantable medical device having a surface coated with an antimicrobial composition that includes a oxidoreductase disposed on the device (e.g. lactate oxidase) that generates hydrogen peroxide upon exposure to a ligand (e.g. lactate), wherein the antimicrobial composition is disposed on the surface of the device so as to allow hydrogen peroxide generated by the oxidoreductase to diffuse away from the oxidoreductase and contact a microorganism attempting to grow on the medical device, thereby inhibiting the growth of the microorganism. In certain embodiments, a surface of the medical device is further coated with a dexamethasone composition. In some embodiments of the invention, the surface of the medical device is that found on a specific portion of a cardiac management system (e.g. one observed to be susceptible to microbial colonization), for example an electronic lead of a pacemaker. In other embodiments of the invention, the surface on an implantable medical devices on found on other components of pacemakers, as well as those surfaces present on a wide variety of implantable medical devices such as cardiovertor defibrillators, neurostimulators, and ECG monitors. Such medical devices typically include one or more leads used for sensing electrical signals in the body, such as intracardiac electrogram (EGM) signals, electrocardiogram (ECG) signals, and electromyogram (EGM) signals. Leads are also used for delivering therapeutic electrical stimulation pulses or for delivering electrical pulses used in electrophysiological mapping or for other diagnostic purposes (see, e.g. U.S. patent application No. 20070154519A1 and U.S. Pat. No. 6,961,610, the contents of which are incorporated by reference)

The methods of the invention can include coating medical device with additional agents designed to inhibit biofilm formation. For example, in some embodiments of the invention, the surface of the device is further coated with a lectin capable of being recognized and bound by a biofilm forming organism. In one such embodiment of the invention, a lectin is used in combination an degradable composition layer that sloughs off of the surface of a medical device that is implanted in a subject, thereby inhibiting the establishment of a biofilm colony by biofilm forming organisms. Such embodiments of the invention therefore provide another coating for a device which further inhibits biofilm formation by having the organisms and biofilm compounds (e.g. the mucopolysaccharides of the biofilm) detach from the device in a manner that facilitates their clearance by the subject's physiological clearance mechanisms such as immunosurveillance and phagocytosis. In addition, as the biofilm components slough off of the device they are made to be more accessible to immune cells (e.g. B cells, T cells, macrophages and the like) that function to further stimulate the host immune response and inhibit the growth of biofilm forming organisms.

In certain embodiments of the invention, a coating is made from one or more degradable and/or erodible materials in order to further hinder an organisms colonization of a surface having that coating. In particular, in certain contexts biofilms are observed to form, if at all, in a relatively short period of time. Consequently, a biodegradable polymer which inhibits the formation of biofilms during the time that devices are most susceptible to microbial colonization (e.g. the first few weeks or months immediately after implantation) can effectively reduce the establishment of a biofilm and/or incidence of biofilm formation. Consequently, certain typical embodiments of the invention utilize devices having a coating composition that includes biodegradable polymers that degrade at a specific rate within the in vivo environment in which they are placed. Illustrative embodiments are those in which greater than 50% (typically greater than 90%) of the biodegradable polymer coating is degraded by 1 week, 2 weeks, 3 weeks, 1 month, 2 months, 3 months etc. after implantation of the medical device.

Another embodiment of the invention is a medical device having a surface coated with a composition comprising an oxidoreductase that produces hydrogen peroxide upon exposure to its ligand (e.g. glucose or lactate) and/or an antimicrobial polymer composition comprising a quaternary amine moiety and/or a method of using such coating to inhibit microbial growth. Optionally a coating on the device further includes a lectin that binds a compound produced by a microorganism capable of forming a biofilm on the surface of the medical device. In such embodiments of the invention, the lectin is typically disposed within (e.g. chemically coupled or entrapped) a biodegradable polymer. Optionally the biodegradable polymer used in such embodiments is a biocompatible polymer that degrades at a predetermined rate within an in vivo environment. Optionally the composition further comprises at least one biocidal agent such as a conventional antibiotic such as a β-lactam antibiotic or an antifungal agent such as a triazole or a polyene antibiotic that binds sterols within the fungal membrane. Typically the device is an implantable device such as a drug delivery pump, a cardiac management device such as a pacemaker, a cochlear implant, an analyte sensing device, a catheter, a cannula or the like.

A variety of permutations of the compositions disclosed herein may be generated by those skilled in the art. For example in certain embodiments of the invention the composition is composed of layers of materials, optionally having different properties. In certain embodiments of the invention, the composition comprises a plurality of polymers, a plurality of oxidoreductases, a plurality of quaternary amine compounds, a plurality of conventional biocidal agents and/or a plurality of lectins (e.g. wheat germ agglutinin and concanavalin A). In some embodiments, a plurality of lectins binds a plurality of compounds produced by a plurality of microorganisms capable of forming a biofilm. In particular it is known in the art that biofilms can comprise multiple interacting microorganisms (see, e.g. Rickhard et al., Applied and Environmental Microbiology, 2000: 431-434 and Rickhard et al., Applied and Environmental Microbiology, 2002: 3644-3650). Alternatively, the plurality of lectins binds a plurality of compounds produced by a single species of microorganism. In other embodiments of the invention, the composition comprises a plurality of polymers. In other embodiments of the invention, the composition comprises a plurality of biocidal agents capable of killing plurality of microorganism species (e.g. both bacterial as well as fungal species). In illustrative embodiments, wherein the lectin and/or the biocidal agent targets a microorganism selected from the group consisting of *Pseudomonas aeruginosa, Streptococcus pneumoniae, Streptococcus viridans, Haemophilus influenzae, Escherichia coli, Staphylococcus aureus, Staphylococcus epidermidis* and *Candida albicans.*

Yet another embodiment of the invention is a method for inhibiting the formation of a biofilm on the surface of a medical device; the method comprising coating the device with a composition comprising an oxidoreductase that produces hydrogen peroxide upon exposure to its ligand and a biodegradable polymer designed to degrade in a manner that sloughs organisms off a surface that they are attempting to colonize. In this method, the biodegradable polymer can entrap the oxidoreductase. Alternatively, the biodegradable polymer can be a separate from the layers having the oxidoreductase. Typically, the biodegradable polymer is selected to degrade at a defined rate within an in vivo environment.

A related embodiment of the invention is a method of making a medical device having a coating that inhibits the microbial colonization of a surface of the device comprising coating the surface with a composition comprising oxidoreductase that produces hydrogen peroxide upon exposure to an analyte such as glucose and an antimicrobial polymer composition comprising a quaternary amine moiety selected for its ability to inhibit the growth of a microorganism. Yet another embodiment of the invention is a method of making a medical device having, a coating that inhibits the microbial colonization of a surface of the device comprising coating the surface with a composition comprising a oxidoreductase that produces hydrogen peroxide upon exposure to a ligand such as glucose and/or an antimicrobial polymer composition comprising a quaternary amine moiety biodegradable polymer and/or a further composition such as a lectin coupled to the biodegradable polymer, wherein the lectin is selected to bind a compound produced by a microorganism capable of forming a biofilm on the surface of the medical device.

In a specific illustrative embodiment of the invention, the surface coated by the compositions is titanium, a material that is commonly used in medical devices and the compositions includes glucose oxidase and a 3-aminopropyltriethoxy silane (a composition having a quaternary amine). In some embodiments of the invention, the device is further coated with a composition comprising a lectin such as concanavalin A, wheat germ agglutinin or a lectin derived from *Helix aspersa, Phaseolus vulgaris* or *Trichamonas vulgaris* (see, e.g. Francoeur et al., Appl Environ Microbiol 2001, 67(9): 4329-34; Neu et al., Microbiology, 2001 147 (pt 2): 299-313; and Appl Environ Microbiol 2000, 66(8): 3487-91). Such lectins are commercially available from a number of sources such as Sigma Chemical Company (e.g. Sigma catalog numbers L9640, L6655, L8629, L9040; and C2010). In this embodiment of the invention, the composition can further include the antibiotic streptomycin. In this embodiment, a lectin can serve to target the biofilm forming organism to a portion of the device that has a biocidal agent (streptomycin) that will kill the organism. In the same manner the lectin therefore facilitates the attachment of the biofilm forming organism to a portion of the device that will slough off in a manner that further inhibits biofilm formation. In such contexts, biofilm formation is inhibited in part by treating the surface of a medical device with a degradable composition that has a greater affinity for biofilms than does the untreated surface of the device.

Various embodiments and aspects of the invention are described in detail below.

Illustrative Compositions for Forming Coatings on Medical Devices

Compositions of the invention can include essentially any one of the wide variety of materials (typically ones which comprise both an oxidoreductase and another compound such as a polymer comprising a quaternary amine or an anti-inflammatory agent such as dexamethasone) that are compatible with medical devices, particularly implanted devices. Polymers may be crosslinked or uncrosslinked, linear or branched, natural or synthetic, thermoplastic or thermosetting, or biostable, biodegradable, bioabsorbable or dissolvable. Embodiments of the invention described herein include various types of polymer coatings for coating implantable medical devices such as cardiac management systems (e.g. pacemakers), analyte sensing devices, drug delivery pumps, cochlear implants, stents, cannulae, and the like that include growth inhibitory agents and/or anti-inflammatory agents. Typically, polymers are applied to the surface of an implantable device by methods such as spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device.

Exemplary polymers that can be used to coat a medical device include but are not limited to the following molecules: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylenetetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Typical polymers for use in connection with the present invention include ethylene-vinyl acetate copolymers (EVA) and polyurethanes and hydrogels. A hydrogel is a highly-interdependent, biphasic matrix consisting of a solid component (usually a polymer, and more commonly a highly cross-linked polymer) that has both hydrophilic and hydrophobic character. Additionally, the matrix has a liquid component (e.g., water) that is retained in the matrix by intermolecular forces. The hydrophobic character provides the matrix with a degree of water insolubility while the hydrophilic character affords water permeability. The polymer portion of the hydrogel will contain functionality which is suitable for hydrogen bonding (e.g., hydroxyl groups, amino groups, ether linkages, carboxylic acids and esters, and the like). Moreover, the affinity for water presented by the hydrogen bonding functionality must be of sufficient degree that the hydrated hydrogel will retain the water within its matrix even upon placement of the hydrogel in a hydrophobic medium such as an oil or lipid matrix. In addition to this binding of water within the hydrogel matrix, the hydrogel should allow water to flow through it when placed in an aqueous environment. Exemplary hydrogels are disclosed in U.S. Pat. Nos. 6,462,162, 5,786,439, and U.S. Pat. No. 5,770,060 which are incorporated herein by reference.

Hydrogels used in coating the implantable devices typically include a polyurea, a polyurethane or a polyurethane/polyurea combination. As used herein, the term "polyurethane/polyurea" refers to a polymer containing urethane linkages, urea linkages or combinations thereof. Typically, such polymers are formed by combining diisocyanates with alcohols and/or amines. For example, combining isophorone diisocyanate with PEG 600 and 1,4-diaminobutane under polymerizing conditions provides a polyurethane/polyurea composition having both urethane (carbamate) linkages and urea linkages. Such hydrogels are typically prepared from the reaction of a diisocyanate and a hydrophilic polymer, and optionally, a chain extender. The hydrogels can be extremely hydrophilic and can have a water pickup of from about 25% to about 400% by weight, more typically from about 150% to about 400%.

The diisocyanates which are useful in this aspect of the invention are those which are typically used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate) ($H_6$XDI), isophorone diisocyanate (IPDI) and 4,4'-methylenebis(cyclohexyl isocyanate) ($H_{12}$ MDI). In typical embodiments, the diisocyanate is an aliphatic diisocyanate, more typically isophorone diisocyanate, 1,6-hexamethylene diisocyanate, or 4,4'-methylenebis(cyclohexyl isocyanate). A number of these diisocyanates are available from commercial sources such as Aldrich Chemical Company (Milwaukee, Wis., USA) or can be readily prepared by standard synthetic methods using literature procedures.

In some embodiments of the invention, the coat composition includes a polymer designed to degrade in a manner that sloughs organisms off a surface that they are attempting to colonize. A number of such polymers are known in the art and are generally termed biodegradable and/or bioerodable. In this context, at least two types of degradation can occur with such polymers. One type of degradation is bulk degradation, in which the polymer degrades in a fairly uniform manner throughout the matrix. The prevailing mechanism of bulk degradation is hydrolysis of the hydrolytically unstable polymer backbone. First, water penetrates the bulk of the solid polymeric implant, preferentially attacking chemical bonds in the amorphous phase and converting long polymer chains into shorter water-soluble fragments. This results, initially, in a reduction in molecular weight ($M_n$) without an immediate change in physical properties. A second type of degradation is surface erosion, typically called bioerosion. Bioerosion can occur when the rate at which water penetrates the coating of the implant is slower than the rate of the conversion of the polymer into water-soluble materials. Bioerosion results in a thinning of the implant coating over time.

Commonly used biodegradable polymers are typically of the poly(hydroxyacid) type, in particular poly(L-lactic acid), poly(D,L-lactic acid), poly(glycolic acid), and copolymers thereof. A typical copolymer is poly(lactide-co-glycolide), abbreviated as PLGA. These materials are broken down in the body to the non-toxic products lactic acid and glycolic acid, and have been approved by the Food and Drug Administration for use as resorbable sutures, in bone implants, and as controlled release microspheres. Other polymers being utilized include poly(funimaric anhydride) and poly(sebacic anhydride). Mathiowitz, E., Jacob, J. S., Jong, Y. S., Carino, G. P., Chickering, D. E., Chaturvedi, P., Santos, C. A., Vijayaraghavan, K., Montgomery, S., Bassett, M. and Morrell, C., Biologically Erodible Microspheres as Potential Oral Drug Delivery Systems, Nature, 386:410-414, 1997. The use of polymeric microspheres for controlled drug delivery has been the subject of a number of reviews. Langer, R., Cima, L. G., Tamada, J. A. and Wintermantel, E.: "Future Directions in Biomaterials," Biomaterials, 11:738-745, 1990.

Additional illustrative bioerodable and/or biodegradable polymers include polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Typical bioerodable polymers include poly(lactic acid), poly(glycolic acid), poly(lactide), poly(glycolide), poly(lactide-co-glycolide)s, poly(caprolactone), polycarbonates, polyamides, polyanhydrides, poly(amino acid)s, poly(ortho ester)s, polyacetals, polycyanoacrylates, poly(ether ester)s, poly(dioxanone)s, poly(alkylene alkylate)s, copolymers of poly(ethylene glycol) and poly(ortho ester), degradable polyurethanes and copolymers and blends thereof. Illustrative bioerodable polymers are further described in U.S. Patent Application Nos. 20020015720 and 20020034533.

Polymers can be designed to have additional desirable properties such as exhibiting rate controlled release of therapeutic agents or other agents. A wide variety of microencapsulation drug delivery systems have been developed using such polymers for the rate controlled release of therapeutic agents or other agents. For instance, considerable research has been devoted to incorporating therapeutic agents into polyesters such as poly-ϵ caprolactone), poly(ϵ-caprolactone-Co-DL-lactic acid), poly(DL-lactic acid), poly(DL-lactic acid-Co-glycolic acid) and poly(ϵ-caprolactone-Co-glycolic acid) in which release was diffusion controlled. See, for example, Pitt, C. G., Gratzl, M. M., Jeffcoat, A. R., Zweidinger, R., Schindler, A., "Sustained Drug Delivery Systems. II. Factors Affecting Release Rates from Poly(ϵ-caprolac-tone) and Related Biodegradable Polyesters", J. Pharm. Sci., 68, 1534 (1979). Degradation of the polyesters has been reported to proceed by random hydrolytic cleavage of ester linkages by an autocatalytic process with the rate of chain cleavage being influenced by chemical and morphological factors.

As is known in the art, the polymer compositions described herein can be used as a scaffolding which can be manipulated to add additional polymer components, bioactive agents, reactive chemical groups and the like. Various polymers and bioactive agents that can be incorporated into the polymer composition scaffolding are described in detail below. In addition, polymers having organic acid functional groups (e.g. carboxylic acid or sulfonic acid) are illustrative embodiments of this aspect of the invention (see e.g. U.S. Pat. No. 6,231,600). In the present context the term "organic acid group" is meant to include any groupings which contain an organic acidic ionizable hydrogen, such as carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

Polymer having organic acid functional groups, can be included in a first or subsequent aqueous coating composition, and can be selected with due regard for the nature of the substrate to be coated. Typically a polymer in a first coating composition will be selected from homo- and co-polymers including vinylic monomer units, polyurethanes, epoxy resins, and combinations thereof. A polymer in the first coating composition is typically selected from polyurethanes, polyacrylates, polymethacrylates, poly-isocrotonates, epoxy resins, acrylate-urethane co-polymers, and combinations thereof having organic acid functional groups. In a particularly typical embodiment of methods of the invention, a polymer in the first coating composition is selected from homo- and co-polymers having a substantial amount of organic acid functional groups in their structure, which may act as an internal emulsifier. A class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly typical.

The polymer compositions and methods of making and using them that are described herein can be used to incorporate a wide variety of bioactive agents that are known in the art (see e.g., Sigwart et al., J Invasive Cardiol 2001 February; 13(2):141-2; discussion 158-70; Chan et al., Update on Pharmacology for Restenosis, Curr Interv Cardiol Rep. 2001 May; 3(2):149-155; and Hofma et al., Recent Developments in Coated Stents, Curr Intern Cardiol Rep. 2001 February; 3(1):28-36). In typical embodiments of the invention, the bioactive component is a lectin selected to bind an organism capable of establishing biofilms on the surfaces of medical implants. In highly typical embodiments of the invention, coating includes a biocidal agent selected to inhibit the growth of and/or kill organisms capable of establishing biofilms on the surfaces of medical implant.

In addition to an oxidoreductase such as glucose oxidase and a polymer comprising a quaternary amine, some embodiments of the coating compositions of the invention can include a lectin capable of binding to a biofilm forming organism. As used herein, a "lectin" is used according to its art accepted meaning and refers to the wide variety of proteins known in the art as being capable of binding cells such as bacterial and/or yeast cells. For selected general references describing such macromolecules, see, e.g. Callow, J. A. and J. R. Green (eds.) 1992, Perspectives in Cell Recognition, Cambridge Univ. Press, Cambridge; Weis et al., Annu Rev Biochem 1996, 56: 441-473; Inbar et al., Crit. Rev Biotechnol 1997, 17(1): 1-20; Archibald et al., Biochem J 1971, 123(4): 665-667; Costerton et al., 1978, How bacteria stick? Sci. Am. (January) 238: 86-95; Ofek, I. and R. J. Doyle 1994, Bacterial Adhesion to Cells and Tissues, Chapman and Hall, NY.; Pueppke, S. G. 1984. Adsorption of bacteria to plant surfaces, pp. 215-261 in Plant Microbe Interactions, Vol. 1; Pusztai, A. 1991, Plant Lectins. Cambridge Univ. Press, Cambridge; Van Damme, E. J. M. et al. 1998, Handbook of Plant Lectins: Properties and Biomedical Applications, Published Chichester; New York: John Wiley; Van Damme, E. J. M., R. J. Doyle and M. Slifkin eds. c1994; and Lectin-microorganism Interactions, Published New York: M. Dekker the contents of each of which is incorporated herein by reference. In addition, a variety of lectins which bind specific pathogens (e.g. *Pseudomonas, Staphylococcus, Streptococcus, Escherichia* and *Chlamydia* species) are known in the art. For selected references describing such molecules see, e.g. Strathmann et al., J Microbiol Methods 2002, 50(3): 237-248; Akiyama et al., J Dermatol Sci 2002, 29(1): 54-61; Cisar et al., Glycobiology 1995, 5(7): 655-662; Coutino-Rodriguez et al., Arch Med Res 2001, 32(4): 251-257; Aitchison et al., J Med Microbiol 1986, 21(2): 161-167; and Mladenov et al., FEMS Immunol Med Microbiol 2002, 32(3): 249-254, the contents of each of which is incorporated herein by reference.

In addition to an oxidoreductase such as glucose oxidase or lactate oxidase and/or a polymer comprising a quaternary amine, some embodiments of the coat compositions further includes a conventional biocidal agent capable of inhibiting the growth of a biofilm forming organism. As used herein, an "biocidal agent" is any agent that is harmful to biofilm forming microbes, especially pathogenic bacteria. Suitable biocidal agents that may be included in the coating include, but are not limited to, antimicrobials, antibiotics, antimyobacterial, antifungals, antivirals, and the like. Typical antimicrobial agents include but are not limited to the biquanides such as chlorhexidine, polymyxins, tetracyclines, aminoglycosides, rifampicin, bacitracin, neomycin, chloramphenicol, miconazole, quinolones, penicillins, nonoxynol 9, fusidic acid, cephalosporins, mupirocin, metronidazole, cecropins, protegrins, bacteriocins, defensins, nitrofurazone, mafenide, vancomycins, clindamycins, lincomycins, sulfonamides, norfloxacin, pefloxacin, nalidixic acid, oxolinic acid (quinalone), enoxacin, ciprofloxacin, and fusidic acid and combinations thereof. Typical broad-spectrum antimicrobial agents for the present invention include triclosan, chlorhexidine, silver sulfadiazine, silver ions, benzalkonium chloride, and zinc pyrithione, as well as broad-spectrum antibiotics such as quinolones, fluoroquinolones, aminoglycosides and sulfonamides, and antiseptics such as iodine, methenamine, nitrofurantoin, validixic acid and other acidifying agents, including acids extracted from cranberry juice and combinations thereof.

Certain embodiments of the invention include coatings having multiple bioactive agents including more than one lectin and/or more than one biocidal agent. For example, typical embodiments of the invention include coatings having multiple lectins which recognize multiple organisms capable of forming biofilms. In this context, certain embodiment of the invention utilize multiple target biocidal agents such as an antibiotic and an antifungal agent in order to inhibit the formation of biofilms comprising mixed species such as *Candida albicans* and *Staphylococcus epidermidis* (see, e.g. Adam et al., J Med Microbiol 2002 April; 51(4):344-9). Other typical embodiments of the invention include coatings having multiple biocidal agents having differing properties. For example, one embodiment of the invention provides compositions having both a fast-acting antimicrobial agent and a long-lasting antimicrobial agent. The combined effect of the antimicrobial agents reduces microbial infection and resistance.

A number of assays for examining the biocompatibility of various compositions are known in the art. Consequently, any permutation of the inventive compositions disclosed herein can be readily examined to assess its biocompatibility profile. For example, U.S. Pat. No. 4,760,020 describes an in vitro assay for biocompatibility. Johnson et al., J Biomed Mater Res. 1985 May-June; 19(5):489-508 describe biocompatibility test procedures for materials evaluation in vitro. Courey et al., J Biomater Appl 1988 October; 3(2):130-79 describe factors and interactions affecting the performance of polyurethane elastomers in medical devices. Tarnok et al., Cytometry 1999 Feb. 15; 38(1):30-9 describe a rapid in vitro biocompatibility assay of endovascular stents by flow cytometry using platelet activation and platelet-leukocyte aggregation. Geckeler et al., Naturwissenschaften 2000 August; 87(8): 351-4 describe a biocompatibility correlation of polymeric materials using human osteosarcoma cells. The contents of each of these disclosures is incorporated herein by reference. In addition, a number of commercially available biocompatibility assays are known in the art which can be used to examine certain embodiments of the invention, for example the CytoTox 96™ Assay sold by Promega (see, e.g. *Promega Notes Magazine* Number 45, 1994, p. 7).

As noted above, embodiments of the present invention relate to the use of a polymer which prevents the accumulation of microorganisms on a surface coated with the polymer, for example a surface of an implanted medical device where such accumulation has deleterious effects on human and animal health. Typically the polymer is a polyurea-silicone copolymer which comprises a diisocyanate such as 4,4-methylenebis(cyclohexyl isocyanate), a hydrophilic diamine such as O,O'-Bis(2-aminopropyl) polypropylene glycol-block polyethylene glycol-block-polypropylene glycol and a hydrophobic silicone such as bis(3-aminopropyl) terminated poly(dimethylsiloxane). Such polymers can be used directly as an implantable medical device or coated onto implantable medical devices to prevent formation of a biofilm of infectious organisms.

The polymer coating preparations described herein can be prepared by methods typically employed in the art, for example those outlined in the examples below. For example, polymerization of the reactants can be carried out in bulk or in a solvent system. Use of a catalyst is typical, though not required. Suitable catalysts include dibutyltin bis(2-ethylhexanoate), dibutyltin diacetate, triethylamine and combinations thereof. Typically dibutyltin bis(2-ethylhexanoate is used as the catalyst. Bulk polymerization is typically carried out at an initial temperature of about 25° (ambient temperature) to about 50° C., in order to insure adequate mixing of the reactants. Upon mixing of the reactants, an exotherm is typically observed, with the temperature rising to about 90°-120° C. After the initial exotherm, the reaction flask can be heated at from 75° C. to 125° C., with 90° C. to 100° C. being a typical temperature range. Heating is usually carried out for one to two hours. Polymers prepared by bulk polymerization are typically dissolved in dimethylformamide and precipitated from water. Polymers prepared in solvents such as THF can be poured into water at ambient temperatures, then filtered, dried, washed with boiling water and re-dried.

Solution polymerization can be carried out in a similar manner. Solvents which are suitable for solution polymerization include, tetrahydrofuran, dimethylformamide, dimethyl sulfoxide, dimethylacetamide, halogenated solvents such as 1,2,3-trichloropropane, and ketones such as 4-methyl-2-pentanone. Typically, THF is used as the solvent. When polymerization is carried out in a solvent, heating of the reaction mixture is typically carried out for at least three to four hours, and typically at least 10-20 hours. At the end of this time period, the solution polymer is typically cooled to room temperature and poured into DI water. The precipitated polymer is typically collected, dried, washed with hot DI water to remove solvent and unreacted monomers, then re-dried. The dried polymer can be evaluated for water pickup as described for example in U.S. Pat. No. 5,786,439 and U.S. Pat. No. 5,777,060. In certain embodiments of the invention, the hydrogels of the invention will have a water pickup of at least 120%, typically 150% to about 400%, and more typically about 200% to about 400%. An illustrative embodiment of the invention includes a polymer coating having a water pickup of from about 25% to about 400% by weight. In a related embodiment, the polymer coating has a glucose diffusion coefficient of from about $1 \times 10^{-9}$ cm$^2$/sec to about $200 \times 10^{-9}$ cm$^2$/sec, and a ratio of $D_{oxygen}/D_{glucose}$ of from about 5 to about 2000, or optionally, from about 5 to about 200.

As discussed herein, the reactants and reaction conditions used to generate the polymer compositions disclosed herein can be modified to alter the properties of the final polymer composition. For example, properties such as the diffusion coefficients (e.g. the rate at which molecules such as endogenous and exogenous analytes are able to diffuse through the polymer matrix), the rate of degradation of one or more of the polymer components or the rates of the release of a bioactive agent(s) can be manipulated by manipulating the reaction conditions (and hence the final polymer composition properties) used to generate the polymers.

From the above description, it will be apparent to one of skill in the art that the discovery underlying the present invention is the use of polymer compositions such as silicon-containing polymers, such as siloxanes. Siloxanes are a class of both organic and inorganic chemical compounds which consist entirely of silicon, oxygen, and an alkyl group. Chemically they are formulated as R2SiO, where R is an alkyl group. Such silicon-containing polymers can be used in conjunction with (e.g. covalently attached to) other compounds such as hydrophilic polymers, compounds having reactive groups and bioactive compositions for the preparation of coatings in which the movement of a ligand (e.g. glucose) and other reactive molecules (e.g. oxygen) can be controlled by varying the amounts of each component. The coatings produced from these components are typically homogeneous and are useful for coating a number of devices designed for in vivo implantation. Once polymers have been prepared having suitable properties, the polymers can be solubilized in a solvent and used to coat a implantable device.

Preparation of coated implantable devices is typically accomplished by dissolving the dried polymer in a suitable solvent and spin-coating the medical device, typically using, for example, a 5 wt % in 2-propanol solution of the polymer. The selection of other suitable solvents for coating the medical devices will typically depend on the particular polymer as well as the volatility of the solvent. Other suitable solvents include THF, CHCl$_3$, CH$_2$Cl$_2$, DMF or combinations thereof. More typically, the solvent is THF or DMF/CH$_2$Cl$_2$.

A typical method of modulating the properties of the polymer compositions disclosed herein is to control the diffusion coefficient (which relates to the rate at which a compound diffuses through a coating matrix) of the one or more polymer coating layers. In this context, ligand diffusion coefficients can be determined for the coating compositions of the present invention. Methods for determining diffusion coefficients are known to those of skill in the art, and are described for example in U.S. Pat. No. 5,786,439 and U.S. Pat. No. 5,777,060 which are incorporated herein by reference. Depending on the selection of components, the silicon polymer having a quaternary amine moiety will comprise a polyurea, a polyurethane or a polyurethane/polyurea combination. Compositions of the invention can be prepared from biologically acceptable polymers whose hydrophobic/hydrophilic balance can be varied over a wide range to control the ratio of the diffusion coefficient of oxygen to that of glucose, and to, for example, match this ratio to the design requirements of a specific medical device such as an electrochemical glucose sensor intended for in vivo use. Such compositions can be prepared by conventional methods by the polymerization of monomers and polymers noted above. The resulting polymers are soluble in solvents such as acetone or ethanol and may be formed as a membrane from solution by dip, spray or spin coating. In one such coating embodiment, a silicon polymer having a quaternary amine moiety can be formed from a reaction mixture of a diisocyanate, the diisocyanate comprising about 50 mol % of the reactants in the mixture; a hydrophilic polymer which is a member selected from the group consisting of a hydrophilic diol, a hydrophilic diamine and combinations thereof; and a silicone polymer having functional groups at the chain termini. Optionally, the reaction mixture will contain a chain extender.

Diisocyanates which can be used in this aspect of the invention are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6 hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate), isophorone diisocyanate (IPDI) and 4,4'-methylenebis(cyclohexyl isocyanate). In certain embodiments, the diisocyanate is isophorone diisocyanate, 1,6-hexamethylene diisocyanate, or 4,4'methylenebis(cyclohexyl isocyanate). A number of these diisocyanates are available from commercial sources such as Aldrich Chemical Company (Milwaukee, Wis., USA) or can be readily prepared by standard synthetic methods using literature procedures. The quantity of diisocyanate used in the reaction mixture for the present compositions is typically about 50 mol % relative to the combination of the remaining reactants. More particularly, the quantity of diisocyanate employed in the preparation of the present compositions will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), b moles of a silicone polymer having functionalized termini, and c moles of a chain extender, such that x=a+b+c, with the understanding that c can be zero.

A second reactant used in the preparation of the compositions described herein can be a hydrophilic polymer. The hydrophilic polymer can be a hydrophilic diol, a hydrophilic diamine or a combination thereof. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a typical hydrophilic diamine is a "diamino poly(oxyalkylene)" which is poly(alkylene)glycol in which the terminal hydroxyl groups are replaced with amino groups. The term "diamino poly (oxyalkylene" also refers to poly(alkylene)glycols which have aminoalkyl ether groups at the chain termini. One example of a suitable diamino poly(oxyalkylene) is poly(propylene glycol)bis(2-aminopropyl ether). An amount of hydrophilic polymer which is used in the present compositions will typically be about 10% to about 80% by mole relative to the diisocyanate which is used. Optionally, the amount is from about 20% to about 60% by mole relative to the diisocyanate.

Silicone polymers which can be used the present invention are typically linear, have excellent oxygen permeability and essentially no glucose permeability. Optionally, the silicone polymer is a polydimethylsiloxane having one, two or more reactive functional groups. The functional groups can be, for example, hydroxyl groups, amino groups or carboxylic acid groups. In some embodiments, combinations of silicone polymers can be used in which a first portion comprises hydroxyl groups and a second portion comprises amino groups. Optionally, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Silicone polymers can optionally be those having a molecular weight of from about 400 to about 10,000, more typically those having a molecular weight of from about 2000 to about 4000. The amount of silicone polymer which is incorporated into the reaction mixture will depend on the desired characteristics of the resulting polymer from which the biocompatible membrane are formed. For those compositions in which a lower glucose penetration is desired, a larger amount of silicone polymer can be employed. Alternatively, for compositions in which a higher glucose penetration is desired, smaller amounts of silicone polymer can be employed. Typically, for a glucose sensor, the amount of siloxane polymer will be from 10% to 90% by mole relative to the diisocyanate. Optionally, the amount is from about 20% to 60% by mole relative to the diisocyanate.

In one group of embodiments, the reaction mixture for the preparation of biocompatible membranes will also contain a chain extender which is an aliphatic or aromatic diol, an aliphatic or aromatic diamine, alkanolamine, or combinations thereof. Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy) benzene, meta-di(2-hydroxyethoxy)benzene, Ethacure 100® (a mixture of two isomers of 2,4-diamino-3,5-diethyltoluene), Ethacure 300® (2,4-diamino-3,5-di(methylthio)toluene), 3,3'-dichloro-4,4'diaminodiphenylmethane, Polacure® 740M (trimethylene glycol bis(para-aminobenzoate)ester), and methylenedianiline. Incorporation of one or more of the above chain extenders typically provides the resulting biocompatible membrane with additional physical strength, but does not substantially increase the glucose permeability of the polymer. Optionally, a chain extender is used when lower (i.e., 10-40 mol %) amounts of hydrophilic polymers are used. In some compositions, the chain extender is diethylene glycol which is present in from about 40% to 60% by mole relative to the diisocyanate.

Polymerization of the above reactants can be carried out in bulk or in a solvent system. Use of a catalyst is typical, though not required. Suitable catalysts include dibutyltin bis(2-ethylhexanoate), dibutyltin diacetate, triethylamine and combinations thereof. Optionally dibutyltin bis(2-ethylhexanoate is used as the catalyst. Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90°-120° C. After the initial exotherm, the reaction flask can be heated at from 75° C. to 125° C., with 90° C. to 100° C. being an illustrative temperature range. Heating is usually carried out for one to two hours. Solution polymerization can be carried out in a similar manner. Solvents which are suitable for solution polymerization include dimethylformamide, dimethyl sulfoxide, dimethylacetamide, halogenated solvents such as 1,2,3-trichloropropane, and ketones such as 4-methyl-2-pentanone. Optionally, THF is used as the solvent. When polymerization is carried out in a solvent, heating of the reaction mixture is typically carried out for three to four hours.

Polymers prepared by bulk polymerization are typically dissolved in dimethylformamide and precipitated from water. Polymers prepared in solvents that are not miscible with water can be isolated by vacuum stripping of the solvent. These polymers are then dissolved in dimethylformamide and precipitated from water. After thoroughly washing with water, the polymers can be dried in vacuo at about 50° C. to constant weight. Preparation of the membranes can be completed by dissolving the dried polymer in a suitable solvent and cast a film onto a glass plate. The selection of a suitable solvent for casting will typically depend on the particular polymer as well as the volatility of the solvent. Optionally, the solvent is THF, $CHCl_3$, $CH_2Cl_2$, DMF or combinations thereof. More typically, the solvent is THF or DMF/$CH_2Cl_2$ (2/98 volume %) The solvent is removed from the films, the resulting membranes are hydrated fully, their thicknesses measured and water pickup is determined. Membranes which are useful in the present invention will typically have a water pickup of about 20 to about 100%, optionally 30 to about 90%, and more typically 40 to about 80%, by weight.

Oxygen and glucose diffusion coefficients can also be determined and/or controlled for the compositions of the present invention. Methods for determining diffusion coefficients are known to those of skill in the art, and examples are provided for example in U.S. Pat. No. 5,770,060 which is incorporated by reference. Optionally, a membrane formed using the polymerized mixture of the above components will have a glucose diffusion coefficient of from about 1 to about 200·$10^{-9}$ $cm^2$/sec. In certain embodiments, a membrane formed using the polymerized mixture of the above components will have a water pickup of at least 25% and a ratio of $D_{oxygen}/D_{glucose}$ of from about 5 to about 200.

An illustrative method of coating a medical device includes sequentially applying a plurality of relatively thin outer layers of a coating composition comprising a solvent mixture of a polymeric silicone material and crosslinker and, optionally a biologically active species (see, e.g. U.S. Pat. No. 6,358,556). The coatings can be cured in situ and the coated, cured prosthesis can be sterilized in a step that includes typical pretreatment with argon gas plasma and exposure to gamma radiation electron beam, ethylene oxide, steam.

In this context, embodiments of the present invention provides processes for producing a relatively thin layer of biostable elastomeric material in which an amount of biologically active material is dispersed as a coating on the surfaces of a medical device such as a stent. The typical stent to be coated is a self-expanding, open-ended tubular stent prosthesis. Although other materials, including polymer materials, can be used, in the typical embodiment, the tubular body is typically formed of an open braid of fine single or polyfilament metal wire which flexes without collapsing and readily axially deforms to an elongate shape for transluminal insertion via a vascular catheter. The stent resiliently attempts to resume predetermined stable dimensions upon relaxation in situ.

The polymer coating is typically applied as a mixture, solution or suspension of polymeric material and one or more biologically active species dispersed in an organic vehicle or a solution or partial solution of such species in a solvent or vehicle for the polymer and/or biologically active species. Optionally different biological species are placed within different polymer layers. The bioactive material(s) is dispersed in a carrier material which may be the polymer, a solvent, or both. The coating is typically applied as one or more relatively thin layers that are applied sequentially. In some applications the coating may further be characterized as an undercoat and a topcoat. The coating thickness ratio of the topcoat to the undercoat may vary with the desired effect and/or the elution system. Typically these are of different formulations.

In an illustrative embodiment of a device having a plurality of coating layers, the coating on the medical device includes one or more base coatings and a top coating (see, e.g. U.S. Pat. No. 6,287,285). Optionally, the base coat has a binding component and a grafting component, and is used to adhere to the surface of the device and also to bond to the top coat. Specifically, the binding component binds to both the top coat and to the grafting component, and the grafting component adheres to the device surface. Typically, the base coat containing the grafting component and binding component in a suitable carrier such as a solution is first applied to the surface of the device. The base coat is typically polymerized, e.g., exposed to polymerizing agent to polymerize the grafting component, and the grafting component is bonded to the binding component and adhered to the surface of the device to form a base coat on the device. The device is then coated with a top coat containing a desired bioactive agent. The top coat may be applied in a solution which is allowed to evaporate, to form a top coat with a bioactive agent. In another embodiment, the device is coated with a top coat comprising a linking agent, and the linking agent is exposed to the bioactive agent to form a complex therewith, to thereby form the bioactive coating of the invention. Because the top coat bonds to the base coat, the bioactive coating produced will not readily wear off.

Yet another embodiment of the invention includes the conjugation of a bioactive agent to a polymer via a hydrolytically labile bond to increase agent retention in a tissue, and, therefore increase the penetration distance of the bioactive agent in the tissue (see, also U.S. Pat. No. 6,545,681). Typically the bioactive agent conjugate is administered in a controlled-release matrix which comprises a biocompatible second polymer. Optionally the first polymer is water-soluble and the second polymer is not water-soluble. In this context, the polymer compositions of the invention comprise a polymer containing a functional group containing at least one hydrolyzable bond. Such polymer compositions include homo- and co-polymers and blends thereof (a copolymer or blend includes at least one other polymer which may or may not contain hydrolyzable bonds). By "hydrolyzable," "hydrolysis," and the like is meant the ability of water to chemically react with a substance to form two or more new substances. This typically involves ionization of the water molecule as well as splitting of the compound being hydrolyzed, e.g., an ester group of a polyester is hydrolyzed into the corresponding carboxylic acid and alcohol. By "acid-hydrolyzable bonds" and "base-hydrolyzable bonds" it is meant that the hydrolysis of the bond is initiated or catalyzed by an acidic or basic material, respectively. A bond may be both acid and base hydrolyzable. In addition, both types of bonds may be present in the polymer composition. The functional group containing hydrolyzable bonds may be present in the linear portions of the polymer chain (i.e., internal groups) or may be pendant to the polymer chain.

Exemplary functional groups which contain acid-hydrolyzable bonds include ortho-ester and amide groups. Exemplary functional groups which contain base-hydrolyzable bonds include α-ester and anhydride groups. Functional groups which contain both acid- and base-hydrolyzable bonds include carbonate, ester, and iminocarbonate groups. Thus, such exemplary polymers for use in the polymer compositions of the invention include polyesters, cellulose esters, polyester polyurethanes, polyamides, polycarbonates, and polyamino acids. A variety of other functional groups which contain labile bonds are known in the art and can be readily employed in the methods and compositions described herein (see, e.g. Peterson et al., Biochem. Biophys. Res. Comm. 200(3): 1586-1591 (1994) and Freel et al., J. Med. Chem. 43: 4319-4327 (2000)).

A variety of compositions and methods known in the art can be used to generate the compositions having functional groups which contain acid-hydrolyzable bonds disclosed herein. For example, in certain aspects, the present invention provides ortho ester lipids, and derivatives thereof, which upon certain pH conditions, undergo hydrolysis with concomitant or subsequent head group cleavage. As such, the present invention provides polymer compounds which include the compounds of Formula I as shown in U.S. Pat. No. 6,200,599. The compounds of Formula I typically comprise an ortho ester functionality or a derivative thereof. In general, ortho ester functionalities are among the most sensitive moieties toward acid-induced hydrolysis, more acid labile than for instance, acetals or enol-ethers. Although the ortho esters of this embodiment of the invention are typically bicyclic in nature, the compounds of Formula I are not limited as such. Typically, upon a decrease in pH, the ortho esters of the present invention are (i) hydrolyzed and thereafter undergo (ii) intramolecular transesterification with concomitant or subsequent headgroup cleavage. In certain instances, such as when $R^2$ is an alkoxy group and $R^3$ is hydrogen, compounds of Formula I are not bicyclic. However, these compounds retain their 'self-cleaving' feature and ability to participate in the 2-step decomposition process discussed above. In Formula I, A and $A^1$ can be the same or different heteroatom. By changing the nature of the heteroatoms making up the ortho ester functionality, (e.g., replacing an oxygen atom with a sulfur atom) the ortho esters become susceptible to hydrolysis at varying pH. Thus, it is possible to tailor or program the pH value where hydrolysis of the ortho ester will occur. Moreover, incorporation of sulfur enables oxidative means of ortho ester hydrolysis via sulfoxide or sulfone intermediates.

As discussed in U.S. Pat. No. 6,300,458, hydroxypolycarbonates (HPC) offer to the biomedical area additional hydroxyl functional polymers that bind bioactive agents or carbohydrate polymers chemically or via hydrogen bonding to facilitate agent delivery and utility with subsequent biodegradability to acceptable byproducts. In a specific embodiment, the cyclic carbonate (CC) from the monoketal diol of pentaerythritol polymerized in $CHCl_3$ at 60° C. with $Et_2$ Zn catalyst in $CHCl_3$ at 60° C. in 4 hours to a quantitative yield of high molecular weight, crystalline polymer (PCC), melt peak 199° C. and Tg of 99° C. PCC is readily hydrolyzed with 80% acetic acid to the water-insoluble but water-swollen HPC, poly[5,5-bis(hydroxymethyl)-1,3-dioxan-2-one], with $M_w=3.1 \times 10^4$. HPC degrades completely in vitro in <16 hours in PBS-1× buffer (Ph 7.4, 37° C.) to pentaerythritol and presumably $CO_2$. This rapid degradation rate is decreased with random copolymers of HPC with CC, ε-caprolactone, or L-lactide. HPC and PCC may have important biomaterial applications as is and as the copolymers noted above or with ethylene oxide or other desirable comonomers. PCC and CC copolymers have properties attractive to the biomedical area as is or by conversion to the HPC product provided by hydrolysis or by in vivo enzymatic attack.

In this context, embodiments of the present invention include high weight average molecular weight (>5,000) polymers and copolymers of 5,5-bis(hydroxymethyl) 1,3-dioxan-2-one (hereinafter referred to as "BHMDO") and processes for manufacturing these polymers and copolymers. These polymers are biocompatible and useful for a variety of biomedical applications. Such homopolymers are crystalline and have a high melting point (ca 160-190° C.) which provides excellent mechanical properties. At the same time, they are hydrophilic and swellable by water (ca 100% at 37° C.), thereby enhancing biodegradability. The hydroxyl groups permit easy modification, an important advantage over non-hydrophilic biopolymers. For example, one can chemically bond a agent by an appropriate hydroxyl group reaction to form a hydrolytically labile bond or with a small peptide link cleavable by body enzymes along with a chemically bonded bioactive agent to target the anatomy with the appropriate agent. The hydroxyl groups provide hydrogen bonding with carbohydrate polymers, including nucleic acids, and proteins, which also facilitate direction of these polymers, as is or modified, to specific cites for therapeutic purposes. Properties can be varied widely via copolymers (generally from about 1% up to about 99% BHMDO) to change properties and permit diverse biomedical applications.

Related embodiments of the present invention provide erodible yet biocompatible polymers with desirable mechanical properties. In this context, the polymers HPC and PLC may also be attractive materials for temporary scaffolds or coatings. A feature of these polymers is their tendency to undergo surface erosion. Heterogeneous hydrolysis theoretically would better preserve the mechanical strength and physical integrity of the matrix during biodegradation, which is highly desirable in terms of predictable performance. To maximize control over the release process, it is desirable to have a polymeric system which degrades from the surface and deters the permeation of the agent molecules. Achieving such a heterogeneous degradation requires the rate of hydrolytic degradation on the surface to be much faster than the rate of water penetration into the bulk. A typical embodiment is a polymer composition having a hydrophobic backbone and a water labile linkage.

Related embodiments of the invention provide additional compositions and method for releasing a bio-active agent or a agent within a biological environment in a controlled manner. One such composition is a dual phase polymeric agent-delivery composition comprising a continuous biocompatible gel phase, a discontinuous particulate phase comprising defined microparticles and an agent to be delivered (see, e.g. U.S. Pat. No. 6,287,588). Typically in such embodiments, a microparticle containing a bio-active agent is releasably entrained within a biocompatible polymeric gel matrix. The bio-active agent release may be contained in the microparticle phase alone or in both the microparticles and the gel matrix. The release of the agent is prolonged over a period of time, and the delivery may be modulated and/or controlled. In addition, a second agent may be loaded in some of the microparticles and/or the gel matrix.

In such embodiments of the invention, a main mechanism of in vivo degradation of the polymers is by hydrolytic degradation in which endogenous enzymes may also play a role (see, e.g. Meyers et al., J. Med. Chem. 2000, 43, 4319-4327). Important factors influencing hydrolytic degradation include water permeability, chemical structure, molecular weight, morphology, glass transition temperature, additives, and other environmental factors such as pH, ionic strength, site of implantation, etc. The duration of sustained delivery can be adjusted from few days up to one year by a person of ordinary skill in the art through proper selection of polymer and fabrication method.

Embodiments of the invention include those in which the release of one or more biologically active agents is multiphasic. For example, this release can comprise an initial burst or, immediate release of an agent present at or near the surface of the coating layer, a second phase during which a release rate is slow or sometime no bio-active agent is released, and a third phase during which most of the remainder of the biologically active agent (or another bioactive agent) is released as erosion proceeds. Any agent, as long as it is suitable for incorporation into a polymer matrix (e.g. via microencapsulation in a microparticle), as is known in the art, can utilize the delivery system described by the current invention.

As noted above, this invention is applicable to bio-active agents of all types including lectins and growth inhibitory agents. In some instances, the functionality or physical stability of bioactive agent can also be increased by the addition of various additives to aqueous solutions or suspensions of the polypeptide or protein agent. Additives, such as polyols (including sugars), amino acids, surfactants, polymers, other proteins and certain salts may be used. These additives can readily be incorporated into the microparticle/polymer gel system of the present invention, which will then undergo a gelation process.

Essentially any medical device which experiences microbial colonization and/or biofilm formation and/or encrustation is appropriate for the practice of the present invention, including analyte sensing devices such as electrochemical glucose sensors, drug delivery devices such as insulin pumps, devices which augment hearing such as cochlear implants, urine contacting devices (for example, urethral stents, urinary catheters), blood contacting devices (including cardiovascular stents, venous access devices, valves, vascular grafts, hemodialysis and biliary stents), and body tissue and tissue fluid contacting devices (including biosensors, implants and artificial organs). Medical devices include but are not limited to permanent catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, cerebral and spinal shunts, heart valves, heart assist devices (e.g., left ventricular assist devices), pacemaker capsules, incontinence devices, penile implants, small or temporary joint replacements, urinary dilator, cannulae, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field. Medical devices also include any device which may be inserted or implanted into a human being or other animal, or placed at the insertion or implantation site such as the skin near the insertion or implantation site, and which include at least one surface which is susceptible to colonization by biofilm embedded microorganisms. Medical devices also include any other surface which may be desired or necessary to prevent biofilm embedded microorganisms from growing or proliferating on at least one surface of the medical device, or to remove or clean biofilm embedded microorganisms from the at least one surface of the medical device, such as the surfaces of equipment in operating rooms, emergency rooms, hospital rooms, clinics, and bathrooms.

The medical devices may be formed of any suitable metallic materials or non-metallic materials known to persons skilled in the art. Examples of metallic materials include, but are not limited to titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex (polytetrafluoroethylene), Dacron™ (polyethylene tetraphthalate), Teflon (polytetrafluoroethylene), latex, elastomers and Dacron™ sealed with gelatin, collagen or albumin, and derivatives or combinations thereof. The medical devices include at least one surface for applying the biofilm inhibiting composition. Typically, the biofilm inhibiting composition is applied to the entire portion of the medical device that is accessible to biofilm forming organisms.

As shown above, the polymer compositions of the present invention are useful with a variety of implantable devices. The present invention depends not on the configuration of the implantable device, but rather on the use of the inventive membranes to cover or encapsulate the device elements. Typical embodiments of the present invention include a therapeutic, biocompatible coating over the susceptible surface of a device substrate. The term "susceptible surface" as used herein refers to any surface whether in an industrial or medical setting, that provides an interface between an object and the fluid. A surface, as understood herein further provides a plane whose mechanical structure, without further treatment, is compatible with the adherence of microorganisms. Microbial growth and/or biofilm formation with health implications can involve those surfaces in all health-related environments.

Susceptible surfaces further include the inner and outer surfaces of pieces of medical equipment, medical gear worn or carried by personnel in the health care settings and protective clothing for biohazard or biological warfare applications. Such surfaces can include counter tops and fixtures in areas used for medical procedures or for preparing medical apparatus, tubes and canisters used in respiratory treatments, including the administration of oxygen, solubilized drugs in nebulizers, and anesthetic agents. Additional surfaces include those surfaces intended as biological barriers to infectious organisms such as gloves, aprons and faceshields. Surfaces in contact with liquids are particularly prone to microbial growth and/or biofilm formation. As an example, those reservoirs and tubes used for delivering humidified oxygen to patients can bear biofilms inhabited by infectious agents. Dental unit waterlines similarly can bear biofilms on their surfaces, providing a reservoir for continuing contamination of the system of flowing and aerosolized water used in dentistry.

In accordance with the invention, a method for preventing, inhibiting or eliminating the growth, dissemination and/or accumulation of microorganisms on a susceptible surface (including but not limited to the formation of biofilms) comprises the step of contacting such surface with an composition of the invention, with an amount sufficient to prevent, inhibit or eliminate such growth, dissemination and/or accumulation, i.e., with an effective amount.

The hydrogels described herein are particularly useful with a variety of implantable devices for which it is advantageous to provide a surrounding water layer. Glucose sensors which utilize, for example, glucose oxidase to effect a reaction of glucose and oxygen are known in the art, and are within the skill in the art to fabricate. See, for example, U.S. Pat. Nos. 5,165,407, 4,890,620, 5,390,671 and 5,391,250, the disclosures of each being incorporated herein by reference. For example, sensors for monitoring glucose concentration of diabetics are described in Shichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

Various patents, patent applications, journal articles etc. are cited throughout the specification (e.g. U.S. Pat. No. 6,475,434 or U.S. Patent Application No. 20030031644). The disclosures of all citations in the specification are expressly incorporated herein by reference.

EXAMPLES

Example 1

Evaluation of Antimicrobial Enzyme Coatings Against *Staphylococcus Epidermidis*

Polymeric materials such as medical devices are frequently treated with incorporated or bound antimicrobial agents. In contrast to eluting antimicrobial treatments, surface-bound antimicrobials require contact with the microbial cell for maximal activity. This experiment involved the use of agar slurry inoculum vehicle that provides uniform contact of the inoculum with the treated surfaces. Various bioactive surfaces with glucose oxidase were evaluated for its antimicrobial activity against *Staphylococcus epidermidis*.

Figure 3:
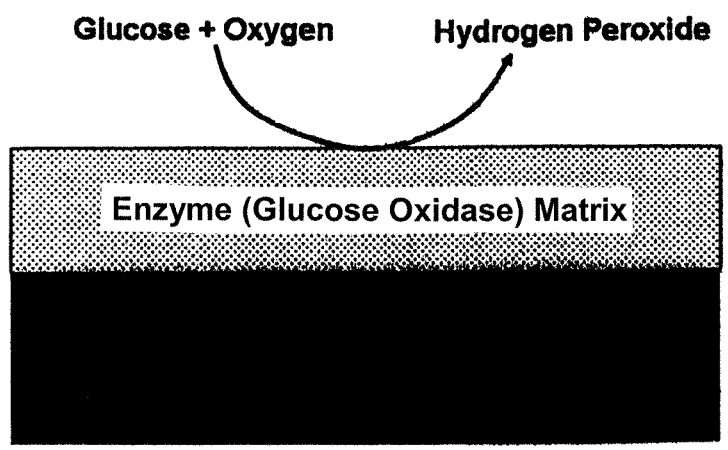
FIG. 3 provides a schematic of antimicrobial GOx enzyme coating on implantable medical device.
Figure 4A:
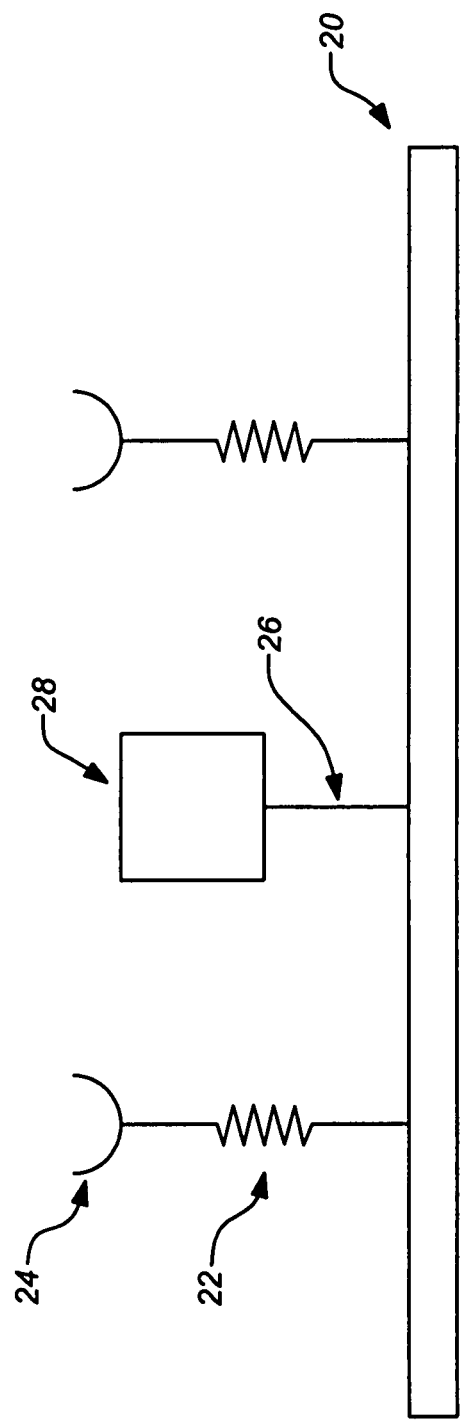
FIGS. 4A-4C provide illustrations of a surface of a medical device coated with a composition of the invention. The embodiment of the invention that is illustrated by these figures includes a lectin capable of being recognized and bound by a biofilm forming organism. The lectin shown in this figure is disposed in a coating that is degradable. In addition, in this embodiment of the invention the surface of the medical device includes a coating having an agent that inhibits the growth of the organism.
Figure 4B:
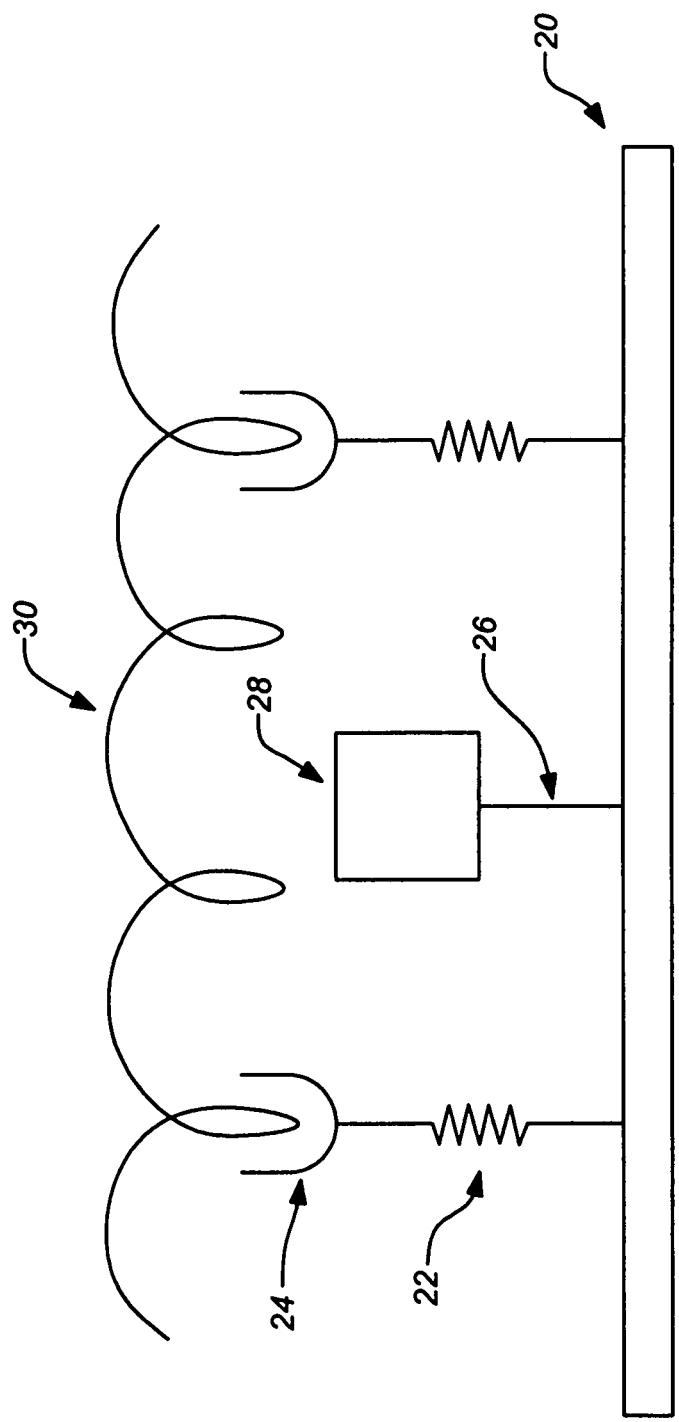
Figure 4C:
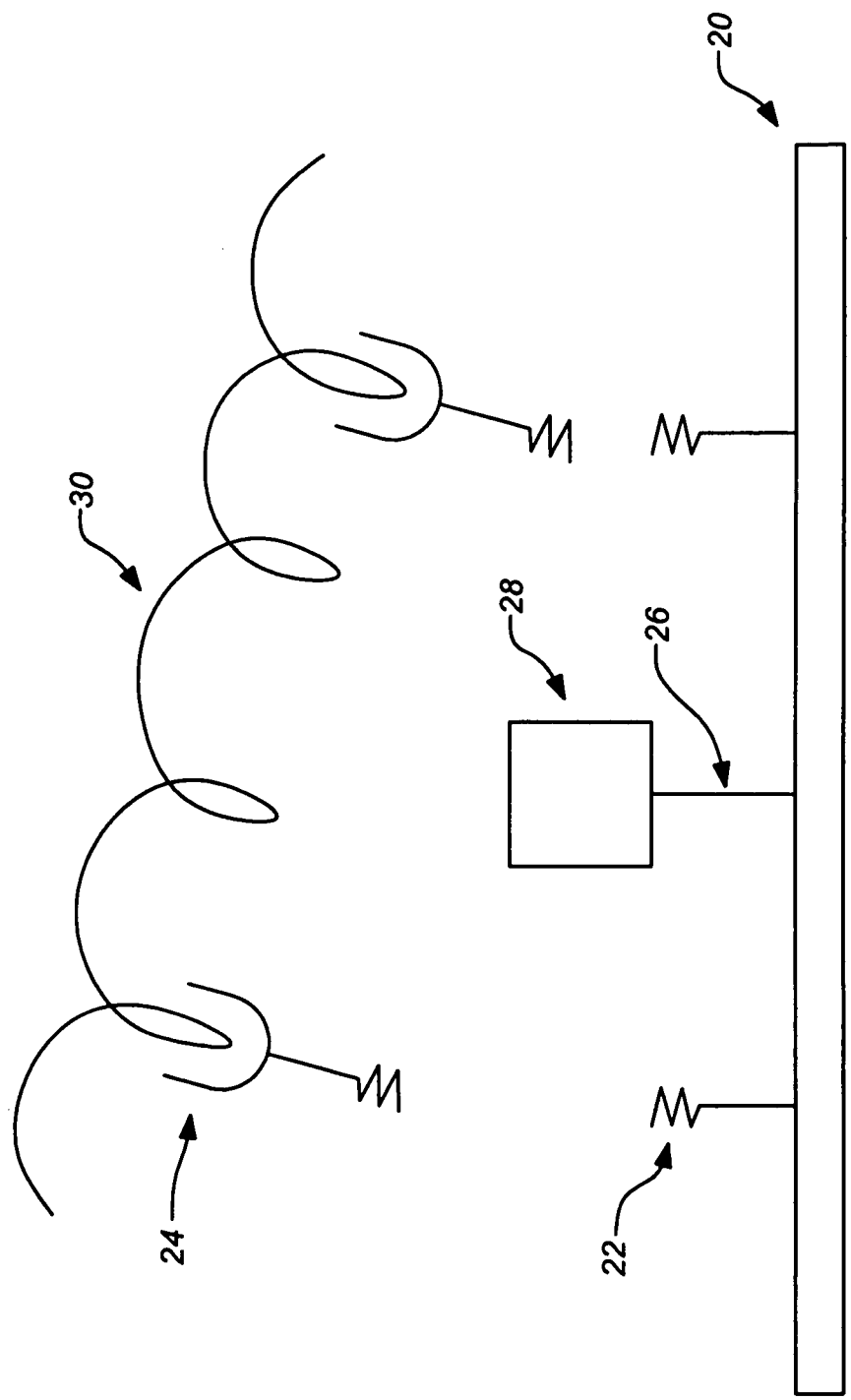

An evaluation was conducted to test the anti-microbial activity of titanium test surfaces coated with glucose oxidase. The surfaces were evaluated on their ability to reduce the bacterial count (log reduction) from the initial inoculum count after 24 hour exposure of the bacterial inoculum with the test surfaces. Results were evaluated as follows:

<2.00 log reduction=low antimicrobial activity
2.00 to 3.00 log reduction=intermediate antimicrobial activity
>3.00 log reduction=high antimicrobial activity As illustrated by the results in this example, an antimicrobial enzyme such as glucose oxidase (GOx), can be coated on an implantable medical device to prevent infectious biofilm formation once it is implanted in human or animal. Enzyme can be immobilized by chemical or physical fixation with biological and synthetic polymers. Glucose oxidase interacts with glucose to release antiseptic hydrogen peroxide to kill any infectious microorganism once the device is implanted as shown in FIG. 3. The antimicrobial activity of glucose oxidase can be manipulated in a control way via different surface immobilization techniques of glucose oxidase on implantable medical devices.

Methods and Materials for Microbial Evaluation

| | |
|---|---|
| 3-Aminopropyltriethoxy Silane, Adhesion Promotor (AP) Brush | UCT |
| Polyurea-Silicone Glucose Limiting Membrane (GLM) | |
| Glucose Oxidase (Gox), 80000 unit | Calzyme |
| Glutaraldehyde, Grade I, 25% in water (Glut) | Sigma |
| Albumin, Human Serum, 25% | Baxter |
| tetrahydrofuran (THF), 99.9%, anhydrous, inhibitor-free | Sigma |
| Phosphate Buffer (PBS) | AP8081021 |
| Peroxide detection strips (0.05 ppm-100 ppm) | WaterWork |
| TWEEN 40 | SIGMA |
| *Staphylococcus epidermidis* (ATCC 35984) | |
| Tryptic Soy Broth | |
| Tryptic Soy Agar Plates | |
| Agar-Agar | |
| NaCl | |
| Glucose | |
| Neutralizing broth-Tryptic Soy Broth | |
| Sonicating waterbath, 47 Khz. | |

Sample Preparation
Group 1: Bare Ti disc-AP-GOx-GLM.

Titanium discs were cleaned with isopropyl alcohol and AP was applied on one side of ti disc with brush and then let cure for 2 hrs at RT this was then repeated on the opposite side of Ti disc. A 30 ku GOx solution was prepared by dissolving 40 μl of tween 40 in 1 ml of PBS. HSA and then GOx are mixed to make a GOx solution that is crosslinked on both sides of the disc using glutaraldehyde. After crosslinking, the disc is then rinsed and coated with polyurea-silicone polymer in THF dispensed and let cure for 15 min. The disc is then rinsed and let air dry.

Group 2: Bare Ti disc-AP-GOx-AP-GLM

Repeat application as GOx as noted above. Apply AP on one side of Ti disc with brush for both sides. Let cure for 2 hrs at rt. The disc is then rinsed and coated with polyurea-silicone polymer in then dispensed and let cure for 15 min. The disc is then rinsed and let air dry.

Group 3 Bare Ti Disc
Group 4 Polyurethane 55D

Antimicrobial Test Procedure 1.1. Grow an 18 hr bacterial culture at 37° C. in Tryptic soy broth.
1.2. Prepare an agar slurry by dissolving 0.85 g NaCl, 0.1 g glucose and 0.3 g agar-agar in 100 ml of demonized water. Heat on hot plate until agar dissolved. Autoclave sterilized.
1.3. Adjust bacterial suspension to $1-5 \times 10^8$ cells/ml using a 1.0 McFarland turbidity standard (equivalent to $\sim 3 \times 10^8$ cells/mL)
1.4. Dip sterile cotton swab into sterile 0.85% saline to pre-wet surfaces. This facilitates the spreading of the inoculum.
1.5. Transfer 1.0 mL of adjusted bacterial suspension to the agar slurry equilibrated to 44° C.
1.6. Pipette 0.2 mL of the inoculum to each test/control surface.
1.7. Allow agar to gel then placed at 37° C. in a humidified Chamber for 24±2 hours.
1.8. After exposure, transfer each surface to individual tubes containing 10 mL of neutralizing broth.
1.9. Sonicate the tubes for 1 minute followed by a 1 minute vortex.
1.10. Perform ten-fold serial dilutions through $10^{-2}$ dilution.
1.11. Plate 1.0 mL aliquots, in duplicate, of the $10^0$, $10^{-1}$ and $10^{-2}$ dilutions for all samples.
1.12. Calculate colony forming unit (CFU) per carrier:

CFU/carrier=(avg. cell count)×(dilution factor)×(volume of diluent)×(volume inoculated)(volume plated)

Results
In Vitro $H_2O_2$ Release Test

To ensure that sufficient hydrogen peroxide was generated, group 1 discs were put into 20 ml of 100 mg/dl glucose solution in PBS. Amount of $H_2O_2$ generation was measured with $H_2O_2$ detection strips. Five discs were tested.

| Time | PPM | Delamination |
|---|---|---|
| 0 | <0.05 ppm | No |
| 5 min | 5 ppm | No |
| 30 min | 25 ppm | No |
| 1 hr | 25 ppm | No |
| 2 hrs | 25 ppm | No |
| Over Night | 25 ppm | Yes Three out of five discs' GLM were delaminated from the disc. |

1.13. Antimicrobial Activity

| | Initial Suspension = 9.6 × 10^5 CFU/ml | | | | |
|---|---|---|---|---|---|
| | Dilution | | | | Log |
| samples | 10^0 | 10^-4 | AVG CFU | CFU/carrier | Log | reduction |
| Group 1 | 0, 0 | | <1 | <10 | <1 | 5.71 |
| Group 2 | 0, 0 | | <1 | <10 | <1 | 5.71 |

-continued

| | Initial Suspension = 9.6 × 10^5 CFU/ml | | | | | |
|---|---|---|---|---|---|---|
| | Dilution | | | | | Log |
| samples | 10^0 | 10^-4 | AVG CFU | CFU/carrier | Log | reduction |
| Group 3 | 55, 48, 52, 39, 57, 54 | | 51 | $5.10 \times 10^5$ | 5.71 | no reduction |
| Group 4 | 29, 34 | | 32 | $1.26 \times 10^5$ | 5.10 | no reduction |

2. Conclusion

The glucose oxidase coating releases hydrogen peroxide in presence of glucose. The antimicrobial test demonstrated the glucose oxidase coated titanium had greater than 5.71 log reduction in bacterial colonization compared to the titanium control. However, the coating process needs to be optimized to improve adhesion of the glucose oxidase coating on Titanium substrates.

Example 2

Evaluation of Polyurea-Silicone Copolymer Surfaces for Antimicrobial Activity Against *Staphylococcus Epidermidis*

Polymeric materials such as medical devices are frequently treated with incorporated or bound antimicrobial agents. In contrast to eluting antimicrobial treatments, surface-bound antimicrobials require contact with the microbial cell for maximal activity. This experiment involved the use of agar slurry inoculum vehicle that provides uniform contact of the inoculum with the treated surfaces. Various treated surfaces were evaluated for antimicrobial activity against *Staphylococcus epidermidis*.

An evaluation was conducted to test the anti-microbial potential of titanium test surfaces coated with MiniMed polyurea-silicone copolymer (PSC) technology. The surfaces were evaluated on their ability to reduce the bacterial count (log reduction) from the initial inoculum count after 24 hour exposure of the bacterial inoculum with the test surfaces. Results were evaluated as follows:

<2.00 log reduction=low antimicrobial activity
2.00 to 3.00 log reduction=intermediate antimicrobial activity
> 3.00 log reduction=high antimicrobial activity
Methods and Materials for Microbial Evaluation
Illustrative Materials for Making Polyurea-Silicone Copolymers Tetrahydrofuran (THF), inhibitor free, low moisture.
Poly(propylene glycol-B-ethylene glycol-B-propylene glycol)bis(2 aminopropyl ether) (Average Molecular Weight—600) (CAS #6560536-9) (Aldrich or Huntsman (listed as Jeffamine ED), (G8080033) dried.
Polydimethylsiloxane, aminopropyldimethyl terminated (Estimated Molecular Weight—2200 to 4000 g/ml) (CAS #106214-84-0) dried.
Dibutyltin bis(2-ethylhexanoate).
4,4'-Methylenebis(cyclohexyl isocyanate) (CAS #51 24-30-1).
Distilled or Deionized Water and Nitrogen gas.
Chemical synthetic lab equipment such as a jacketed resin kettles/flasks with inlet/outlet adapters, condensers, mechanical stirrers, syringe pumps, water circulating temperature controllers, syringes, rubber septas, stirring rods & paddles, beakers, magnetic stir bars, magnetic stirrer/hotplate and blenders.

Illustrative Method for Making Polyurea-Silicone Copolymers

In appropriate reaction apparatus mix poly(propylene glycol-P-ethylene glycol-P-propylene glycol), bis(2-aminopropyl terminated) (MW-600) (Jeffamine 600) and polydimethylsiloxane, aminopropyl dimethyl terminated. Warm the reaction vessel and transfer THF minimizing exposure to air. Allow the reaction solution to equilibrate. Add dibutyltin-bis-(2-ethyl hexanoate) and 4,4'-methylenebis(cyclohexyl isocyanate) at a steady rate over the course of about 25 minutes. Upon completion of the addition (~25 minutes), the syringe is flushed with dry THF and added to the reaction. The temperature is then increased and the reaction is allowed to proceed for an additional time, such as 12-18 hours. De-ionized water is then added to the reaction with stirring & heating maintained for an additional time, such as 12-15 hours.

The temperature bath is then shut off allowing the solution to cool. Separately, a blender is filled with deionized or distilled water. The reaction mixture is added to the blender and blended. The mixture is poured through a wire screen and the water discarded. The polymer precipitate is placed back into the blender and washed with clean deionized or distilled water is added. The blender is set on medium for 30 seconds and the mixture is then filtered through a wire screen and the water discarded. Repeat this procedure for the remainder of the reaction mixture. The polymer is divided into two portions and each portion is added to a beaker. The beakers are placed onto hot plate-stirrers and a magnetic stir bar added to each. The mixtures are stirred and heated to a gentle boil and maintained for a time such as 60-120 minutes. The beakers are removed, and the polymer separated by pouring through a fine-mesh screen while hot. The reaction vessel is placed onto a cork ring and filled with water. The water bath is reconnected and the flask heated to about 60° C. for at least one hour to loosen the polymer residuals from the glass. The polymer is patted dry and placed into a large crystallization dish, placed into a vacuum oven and heated under vacuum for a time such as 12-18 hours. The dried polymer is then weighed and placed into a container.

Testing Polyurea-Silicone Copolymer Coated Surfaces
  Group 1: Bare Ti disc-PSC
    PSC was made according to the above-noted protocol.
    Ti discs were cleaned with isopropyl alcohol.
    100 µl of 5% (w/w) PSC in THF dispensed and let cure for 15 min.
    Rinse PSC coated disc at the rate of 0.5 ml/min DiH$_2$O for 30 min.
    Air dry.
  Group 2: Bare Ti disc-(3-Aminopropyltriethoxy Silane (AP)-PSC
    Ti discs were cleaned with isopropyl alcohol.
    Apply AP on one side of Ti disc with brush for both sides.
    Let it cure for 2 hrs at RT.
    100 µl of 5% (w/w) PSC in THF dispensed and let it cure for 15 min.

Rinse PSC coated disc at the rate of 0.5 ml/min DiH$_2$O for 30 min.
Air dry
Group 3 Bare-Ti control
*Staphylococcus epidermidis* (ATCC 35984)
Tryptic Soy Broth
Tryptic Soy Agar Plates
Agar-Agar
NaCl
Neutralizing broth-Tryptic Soy Broth
Sonicating waterbath, 47 Khz.

Procedure

Grow an 18 hr bacterial culture at 37° C. in tryptic soy broth.
Prepare an agar slurry by dissolving 0.85 g NaCl and 0.3 g agar-agar in 100 ml of deionized water. Heat on hot plate until agar dissolved. Autoclave sterilized.
Adjust bacterial suspension to 1-5×10$^8$ cells/mL using a 1.0 McFarland turbidity standard (equivalent to ~3×10$^8$ cells/mL)
Dip sterile cotton swab into sterile 0.85% saline to pre-wet surfaces. This facilitates the spreading of the inoculum.
Transfer 1.0 mL of adjusted bacterial suspension to the agar slurry equilibrated to 44° C.
pipette 0.2 mL of the inoculum to each test/control surface.
Allow agar to gel then placed at 37° C. in a humidified Chamber for 24±2 hours.
After exposure, transfer each surface to individual tubes containing 10 mL of neutralizing broth.
Sonicate the tubes for 1 minute followed by a 1 minute vortex.
Perform ten-fold serial dilutions through 10$^{-2}$ dilution.
Plate 1.0 mL aliquots, in duplicate, of the 10$^0$, 10$^{-1}$ and 10$^{-2}$ dilutions for all samples.
Calculate colony forming unit (CFU) per carrier:

$$CFU/\text{carrier} = \frac{(\text{avg. cell count})(\text{dilution factor})}{\frac{(\text{volume of diluent})(\text{volume inoculated})}{(\text{volume plated})}}$$

Results:
initial Suspension=9.6×10^5 CFU/ml

| MiniMed samples | 10^0 10^-4 | AVG CFU | CFU/carrier | Log | Log reduction |
|---|---|---|---|---|---|
| Group 1 | 0, 0 | <1 | <10 | <1 | 5.71 |
| Group 2 | 0, 0 | <1 | <10 | <1 | 5.71 |
| Group 3 | 55, 48, 52, 39, 57, 54 | 51 | 5.10 × 10^5 | 5.71 | no reduction |

Average of mean logs Ti controls=5.71

CONCLUSION

The PSC coated titanium demonstrated a greater than 5.71 log reduction in bacterial colonization compared to the titanium control.

The invention claimed is:

1. A method of inhibiting growth of a microorganism on a surface of a medical device comprising identifying a susceptible surface on the medical device that is observed to be colonized in vivo by a microorganism when the device is implanted in an individual and coating the surface of the medical device with:
   (a) a first layer comprising an antimicrobial composition that includes an enzyme that generates hydrogen peroxide upon exposure to a ligand of the enzyme; and
   (b) a second layer disposed on the first layer comprising: an antimicrobial composition comprising a polyurea-silicone copolymer having a quaternary amine moiety, wherein:
   the first layer is disposed on the medical device so as to allow hydrogen peroxide generated by the enzyme in the first layer to diffuse away from the enzyme and contact a microorganism attempting to grow on the medical device thereby inhibiting its growth;
   the second layer is formed from a reaction mixture comprising a diisocyanate, a hydrophilic polymer which is selected from the group consisting of a hydrophilic polymer diol, a hydrophilic polymer diamine and combinations thereof, and a siloxane;
   the quaternary amine moiety in the second layer inhibits the growth of a microorganism that contacts the second layer, so that microbial growth is inhibited on the surface of the medical device when the surface is exposed to a microorganism,
   and the device is a glucose sensor comprising a plurality of layers, wherein the plurality of layers include:
   an electrode having an electrochemically reactive surface area;
   an analyte sensing layer that detectably alters electrical current at the electrode in the presence of an analyte; and
   an analyte modulating layer that modulates diffusion of an analyte therethrough.

2. The method of claim 1 wherein the device is implanted in an individual having a pathological condition characterized by hyperglycemia.

3. The method of claim 1, wherein the surface is comprised of titanium.

4. The method of claim 1, wherein the enzyme in the first layer is glucose oxidase.

5. The method of claim 1, further comprising disposing one or more further layers between the first layer and the second layer.

6. The method of claim 5, wherein a further layer disposed between the first layer and the second layer is a composition that promotes adhesion between the first and second layer.

7. The method of claim 1, wherein the method is used to inhibit the growth of a microorganism that is capable of forming a biofilm on the surface of a medical device.

8. A method of inhibiting formation of a biofilm on a medical device that is implanted in an individual having hyperglycemia, the method comprising:
   (a) identifying a surface on the medical device that is observed to be colonized by a biofilm forming microorganism; and
   (b) coating the surface with:
   a first layer that comprises an antimicrobial composition that includes an oxidoreductase that generates hydrogen peroxide upon exposure to a ligand for the oxidoreductase, wherein the amount of hydrogen peroxide generated by the oxidoreductase is proportional to the amount of ligand exposed to the oxidoreductase; and a second layer disposed over the first layer that comprises an antimicrobial composition comprising a polyurea-silicone copolymer, wherein:

the first layer is disposed on the medical device so as to allow hydrogen peroxide generated by the oxidoreductase in the first layer to diffuse away from the oxidoreductase and contact a microorganism attempting to grow on the medical device thereby inhibiting its growth;

the second layer is formed from a reaction mixture comprising a diisocyanate, a hydrophilic polymer which is selected from the group consisting of a hydrophilic polymer diol, a hydrophilic polymer diamine and combinations thereof, and a siloxane; and a quaternary amine moiety in the second layer inhibits the growth of a microorganism that contacts the second layer;

so that formation of a biofilm on the medical device is inhibited when the surface is exposed to the biofilm forming microorganism, wherein the device is a glucose sensor comprising a plurality of layers including:

an electrode having an electrochemically reactive surface area;

an analyte sensing layer that detectably alters electrical current at the electrode in the presence of an analyte;

an adhesion promoting layer that promotes adhesion between one or more layers of the glucose sensor;

an analyte modulating layer that modulates diffusion of an analyte therethrough; and a cover layer that is impermeable to blood glucose, wherein the cover layer includes an aperture.

9. The method of claim 8, further comprising disposing an adhesion promoting layer between the first layer and the second layer.

10. The method of claim 8, wherein the oxidoreductase is glucose oxidase and the method further comprises immobilizing the glucose oxidase on the surface of the medical device using a procedure that results in the glucose oxidase having an oxidoreductase activity that is at least equal to the oxidoreductase activity observed when the glucose oxidase is immobilized on the surface via glutaraldehyde crosslinking.

11. A method of inhibiting microbial growth on a medical device that is implanted in a diabetic individual, the method comprising identifying a susceptible surface on the medical device that is observed to be colonized in vivo by a microorganism when the device is implanted in the diabetic individual and coating the surface of the medical device with at least two antimicrobial compositions, wherein the antimicrobial compositions include:

a first layer comprising a glucose oxidase composition, wherein the glucose oxidase is disposed in the first layer so as to generate hydrogen peroxide upon exposure to glucose in the diabetic individual; and the first layer is disposed on the device so as to allow hydrogen peroxide generated by the glucose oxidase in the first layer to diffuse away from the glucose oxidase and contact a microorganism attempting to grow on the medical device and inhibit its growth; wherein the amount of hydrogen peroxide generated by the glucose oxidase fluctuates in response to fluctuating glucose levels within the diabetic individual; and a second layer disposed on the first layer comprising a polyurea-silicone copolymer composition having a quaternary amine, wherein:

the second layer is formed from a reaction mixture comprising a diisocyanate, a hydrophilic polymer which is selected from the group consisting of a hydrophilic polymer diol, a hydrophilic polymer diamine and combinations thereof, and a siloxane; and the second layer is disposed on the medical device in a location such that the quaternary amine in the second layer inhibits the growth of a microorganism that contacts the second layer; so that microbial growth on the implanted medical device is inhibited, wherein the device is a glucose sensor comprising a plurality of layers, wherein at least one of the layers comprises:

an electrode having an electrochemically reactive surface area;

an analyte sensing layer that detectably alters electrical current at the electrode in the presence of an analyte;

an adhesion promoting layer that promotes adhesion between one or more layers of the glucose sensor;

an analyte modulating layer that modulates diffusion of an analyte therethrough; or a cover layer that is impermeable to blood glucose, wherein the cover layer includes an aperture.

12. A method of inhibiting formation of a biofilm on a medical device that is implanted in an individual having a pathological condition characterized by ischemia, the method comprising:

(a) identifying a surface on the medical device that is observed to be colonized by a biofilm forming microorganism; and (b) coating the surface with:

a first layer that comprises an antimicrobial composition that includes an oxidoreductase that generates hydrogen peroxide upon exposure to a ligand for the oxidoreductase;

a second layer disposed on the first layer that comprises an antimicrobial composition comprising a polyurea-silicone copolymer, wherein:

the first layer is disposed on the medical device so as to allow hydrogen peroxide generated by the oxidoreductase in the first layer to diffuse away from the oxidoreductase and contact a microorganism attempting to grow on the medical device thereby inhibiting its growth;

the second layer is formed from a reaction mixture comprising a diisocyanate, a hydrophilic polymer which is selected from the group consisting of a hydrophilic polymer diol, a hydrophilic polymer diamine and combinations thereof, and a siloxane; and a quaternary amine moiety in the second layer inhibits the growth of a microorganism that contacts the second layer;

so that formation of a biofilm on the medical device is inhibited when the surface is exposed to the biofilm forming microorganism, wherein the medical device is a glucose sensor comprising a plurality of layers, wherein at least one of the layers comprises:

an electrode having an electrochemically reactive surface area;

an analyte sensing layer that detectably alters electrical current at the electrode in the presence of an analyte;

an adhesion promoting layer that promotes adhesion between one or more layers of the glucose sensor;

an analyte modulating layer that modulates diffusion of an analyte therethrough; or a cover layer that is impermeable to blood glucose, wherein the cover layer includes an aperture.

13. The method of claim 12, wherein the pathological condition is heart disease.

14. The method of claim 12, wherein the oxidoreductase is lactate oxidase.

15. The method of claim 14, wherein the lactate oxidase is disposed on the medical device in a location such that:
    hydrogen peroxide generated by the lactate oxidase fluctuates in response to fluctuating lactate levels within the individual; and
    hydrogen peroxide generated by the lactate oxidase diffuses away from the lactate oxidase and contacts a microorganism attempting to grow on the medical device so as to inhibit its growth.

\* \* \* \* \*